(12) United States Patent　　(10) Patent No.: US 12,698,515 B2
Tan et al.　　　　　　　　　　 (45) Date of Patent: Aug. 4, 2026

(54) GENETICALLY ENGINEERED BACTERIUM USING GLUCOSE AS SUBSTRATE FOR DE NOVO SYNTHESIS OF VANILLIN AND APPLICATION THEREOF

(71) Applicant: Beijing University of Chemical Technology, Beijing (CN)

(72) Inventors: Tianwei Tan, Beijing (CN); Yingyue Yu, Beijing (CN); Haowen Zhu, Beijing (CN); Jianyu Long, Beijing (CN)

(73) Assignee: Beijing University of Chemical Technology, Beijing (CN)

( * ) Notice: Subject to any disclaimer, the term of this patent is extended or adjusted under 35 U.S.C. 154(b) by 0 days.

(21) Appl. No.: 18/627,530

(22) Filed: Apr. 5, 2024

(65) Prior Publication Data

US 2024/0318209 A1　　Sep. 26, 2024

(30) Foreign Application Priority Data

Sep. 14, 2023　(CN) ......................... 202311181895.9

(51) Int. Cl.
| | |
|---|---|
| *C12N 9/02* | (2006.01) |
| *C12N 1/205* | (2026.01) |
| *C12N 9/10* | (2006.01) |
| *C12N 9/12* | (2006.01) |
| *C12N 9/14* | (2006.01) |
| *C12P 7/22* | (2006.01) |
| *C12R 1/15* | (2006.01) |

(52) U.S. Cl.
CPC ................ *C12P 7/22* (2013.01); *C12N 1/205* (2021.05); *C12N 9/0008* (2013.01); *C12N 9/1007* (2013.01); *C12N 9/1022* (2013.01); *C12N 9/1029* (2013.01); *C12N 9/1085* (2013.01); *C12N 9/1288* (2013.01); *C12N 9/14* (2013.01); *C12R 2001/15* (2021.05); *C12Y 102/99006* (2013.01); *C12Y 201/01014* (2013.01); *C12Y 202/01001* (2013.01); *C12Y 203/01031* (2013.01); *C12Y 205/01006* (2013.01); *C12Y 205/01054* (2013.01); *C12Y 207/08007* (2013.01); *C12Y 303/01001* (2013.01)

(58) Field of Classification Search
CPC ... C12P 7/22; C12P 7/24; C12N 1/205; C12N 9/0008; C12N 9/1007; C12N 9/1022; C12N 9/1029; C12N 9/1085; C12N 9/1288; C12N 9/14; C12N 1/20; C12N 9/0006; C12N 9/10; C12N 9/88; C12N 9/93; C12N 15/52; C12R 2001/15; C12R 2001/28; C12Y 102/99006; C12Y 201/01014; C12Y 202/01001; C12Y 203/01031; C12Y 205/01006; C12Y 205/01054; C12Y 207/08007; C12Y 303/01001; C12Y 201/01

See application file for complete search history.

(56) References Cited

U.S. PATENT DOCUMENTS

| | | | |
|---|---|---|---|
| 2019/0077741 A1 | 3/2019 | Lee et al. | |
| 2019/0249207 A1* | 8/2019 | Toyazaki | ............. C12N 9/1205 |
| 2022/0049235 A1 | 2/2022 | Wang et al. | |
| 2022/0162546 A1 | 5/2022 | Xu et al. | |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Kim et al., Frontiers in Bioengineering and Biotechnology vol. 10, article 880277, pp. 1-16, 2022.*
Kunjapur et al., Journal of the American Chemical Society 136:11644-11654, 2014.*
Tsuge et al., Appl. Microbiol. Biotechnol. 100:2685-2692, 2016.*
CNIPA, Notification to grant patent right for Chinese application 202311181895.9, Nov. 14, 2023.

* cited by examiner

*Primary Examiner* — Delia M Ramirez
(74) *Attorney, Agent, or Firm* — Hemisphere Law, PLLC

(57)　　ABSTRACT

The present invention discloses a genetically engineered bacterium using glucose as a substrate for de novo synthesis of vanillin and an application thereof, which belongs to the technical field of gene recombination and metabolic engineering. The genetically engineered bacterium using the glucose as the substrate for de novo synthesis of vanillin disclosed by the present invention is recombinant *Corynebacterium glutamicum* modified by chassis microorganisms and including a vanillin synthesis module and a methyl cyclic regeneration module. The genetically engineered bacteria constructed by the present invention are safe and non-toxic, can use the glucose for de novo synthesis of natural vanillin, and is low in production cost, high in yield, and promising in application prospect.

2 Claims, 6 Drawing Sheets

Specification includes a Sequence Listing.

GENETICALLY ENGINEERED BACTERIUM USING GLUCOSE AS SUBSTRATE FOR DE NOVO SYNTHESIS OF VANILLIN AND APPLICATION THEREOF

CROSS REFERENCE TO RELATED APPLICATIONS

This patent application claims the benefit and priority of Chinese Patent Application No. 2023111818959 filed on Sep. 14, 2020, the disclosure of which is incorporated by reference herein in its entirety as part of the present application.

REFERENCE TO SEQUENCE LISTING

The substitute sequence listing is submitted as a XML file filed via EFS-Web, with a file name of "Substitute Sequence_Listing. XML", a creation date of Jul. 7, 2025, and a size of 157,918 bytes. The substitute sequence Listing filed via EFS-Web is a part of the specification and is incorporated in its entirety by reference herein.

TECHNICAL FIELD

The present invention relates to the technical field of gene recombination and metabolic engineering, and more particularly to a genetically engineered bacterium using glucose as a substrate for de novo synthesis of vanillin and an application thereof.

BACKGROUND

Vanillin is an aromatic compound with hydroxyl, aldehyde and oxymethyl substituent groups; and the CAS number is 121-33-5, the molecular formula is $C_8H_8O_3$, and the molecular weight is 152.15. The vanillin is usually a white or light yellow crystal with a melting point of 81-83° C. and a boiling point of 284-285° C., and is difficult to dissolve in water and soluble in organic solvents such as methanol. As an important aromatic compound, the vanillin is wide in use. The vanillin can not only be used as a food additive for a variety of foods in life, but also can be used in cosmetics such as perfume and daily necessities such as soap and toothpaste to stabilize and enhance fragrance. Furthermore, the vanillin is also used for producing products such as plastics, rubber sterilizing agents, electroplating agents, conductive agents and the like in industry. In recent years, the vanillin has been widely used in the medical field to produce various pharmaceutical intermediates, and vanillin may become the most valuable aromatic compound in the medical field.

As a big producer and user of vanillin, the annual demand of the vanillin in China reaches 2350 tons, and the demand still increases year by year. The vanillin produced in China is not only for domestic use, but also is exported to Europe, America, Southeast Asia and other countries, enjoying a good reputation in the world. Based on the above situation, producing the vanillin by biological fermentation is a promising production method, which can more efficiently obtain the compound from cheap sugar. It is already reported in multiple literatures that the vanillin is synthesized by microbial fermentation, but the microbial fermentation has the defect of low yield. The biological de novo synthesis of vanillin was first reported in the de novo synthesis of vanillin in *Schizosaccharomyces pombe* and *Saccharomyces cerevisiae* with protocatechuic acid as an intermediate, but the yield of the vanillin was only 65 mg/L and 45 mg/L (Hansen E H, et al. De novo biosynthesis of vanillin in fission yeast (*Schizosaccharomyces pombe*) and baker's yeast (*Saccharomyces cerevisiae*). [J].Applied & Environmental Microbiology, 2009, 75 (9): 2765-74). It was reported by Ni, et al. that 19.3 mg/L vanillin was synthesized de novo in *Escherichia coli* with ferulic acid as an intermediate and glucose as a substrate, but the yield of vanillin was still very low. (Ni J, et al. Mimicking a natural pathway for de novo biosynthesis: natural vanillin production from accessible carbon sources[J]. Rep, 2015, 5 (1): 13670). Chen Z, et al. reported that 240.69 mg/L of vanillyl alcohol was synthesized de novo in *Escherichia coli* (Chen Z, et al. Establishing an Artificial Pathway for De Novo Biosynthesis of Vanillyl Alcohol in *Escherichia coli*[J]. Acs Synthetic Biology, 2017: acssynbio. 7b00129). Then Yang et al. reported that 559.4 mg/L of vanillyl alcohol was synthesized de novo in a shake flask with glucose as a substrate in a way of *Escherichia coli* mix (Yang M, Meng H, Li X, et al. Coculture engineering for efficient production of vanillyl alcohol in *Escherichia coli* [J].aBIOTECH, 2022, 3 (4): 9), but the vanillyl alcohol is an aldehyde reduction product of vanillin, and has quite different product characteristics from vanillin. In recent years, Kim et al. reported that 310 mg/L vanillin was synthesized de novo in *Corynebacterium glutamicum* from glucose via an intermediate hydroxybenzoic acid, the de novo synthesis yield of vanillin was greatly increased (Kim H S, et al. Engineered *Corynebacterium glutamicum* as the Platform for the Production of Aromatic Aldehydes[J]. Frontiers in Bioengineering and Biotechnology, 2022, 10:880277), but there is still a certain gap from industrial scale-up production.

Therefore, providing a genetically engineered bacterium using glucose as a substrate for de novo synthesis of vanillin and an application thereof is an urgent problem to be solved by those skilled in the art.

SUMMARY

In view of this, the present invention provides a genetically engineered bacterium using glucose as a substrate for de novo synthesis of vanillin and an application thereof, which researches and develops an efficient pathway of biological de novo synthesis of vanillin for problems of the existing biological de novo synthesis of vanillin, and constructs a non-toxic food safe engineered strain capable of using cheap substrates such as glucose to produce the natural vanillin.

A purpose of the present invention is to provide a genetically engineered bacterium for synthesizing vanillin. The strain is safe and non-toxic and can use a microbial fermentation method to produce the vanillin, which has low production cost.

Specifically, a genetically engineered bacterium using glucose as the substrate for de novo synthesis of vanillin is provided; and the genetically engineered bacterium is a recombinant *Corynebacterium glutamicum* modified by genome and including a vanillin synthesis module and a methyl cyclic regeneration module.

The modification of chassis microorganism is to take *Corynebacterium glutamicum* as an original strain to knock out pcaHIG (protocatechuate 3,4-dioxygenase subunit, protocatechuate 3,4-dioxygenase subunit beta (pcaH), protocatechuate 3,4-dioxygenase subunit alpha (pcaG)), van (vanillate demethylase), vdh (vanillin dehydrogenase) and fud (alcohol dehydrogenase (NADP+), and Zn-dependent alcohol dehydrogenases) genes.

The vanillin synthesis module expresses a transketolase gene, a 3-deoxy-7-phosphoheptulonate synthase gene, an O-methyltransferase gene, a Carboxylic acid reductase gene and a 4'-phosphopantetheinyl transferase gene.

The transketolase can efficiently enhance the synthesis of E4P in an HMP pathway, and increase the yield of DAHP. The 3-deoxy-7-phosphoheptulonate synthase helps PEP and E4P to synthesize DAHP. The O-methyltransferase catalyzes protocatechuic acid to generate vanillic acid. The Carboxylic acid reductase catalyzes the vanillic acid to be reduced into vanillin. Because the carboxylic acid reductase expressed by *Corynebacterium glutamicum* is an apoenzyme, the carboxylic acid reductase becomes a whole enzyme under the translational phosphorylation modification of 4'-phosphopantetheinyl transferase.

The methyl cyclic regeneration module expresses a 5-methyltetrahydropteroyltriglutamate-homocysteine methyltransferase gene, an S-adenosylmethionine synthase gene, a homoserine O-acetyltransferase gene and an adenosylhomocysteinase gene.

The homoserine O-acetyltransferase transfers acyl groups of coenzyme A (CoA) or succinyl-CoA to hydroxyl oxygen of homoserine, so that the homoserine is acetylated to form O-acetyl-1-homoserine, preparing for subsequent vulcanization. The strain transforms O-acetyl-1-homoserine to L-homocysteine. The 5-methyltetrahydropteroyltriglutamate-homocysteine methyltransferase helps catalyze the transfer of methyl from 5-methyltetrahydrofolate to L-homocysteine, leading to the formation of methionine, and catalyze the reaction between 5-methyl tetrahydropteroyl tri-L-glutamic acid and L-homocysteine to generate L-methionine and tetrahydropteroyl tri-L-glutamic acid. The S-adenosylmethionine synthase ATP catalyzes the reaction between ATP and water and L-methionine to generate diphosphate, phosphate and S-adenosyl-L-methionine. The adenosylhomocysteinase catalyzes the reaction between water and S-adenosyl-L-homocystein to generate adenosine and L-homocysteine.

Further, the transketolase gene includes an endogenous *Corynebacterium glutamicum* transketolase gene tktA and an optional exogenous transketolase gene.

The 3-deoxy-7-phosphoheptulonate synthase gene includes an endogenous *Corynebacterium glutamicum*3-deoxy-7-phosphoheptulonate synthase gene aroG and an optional exogenous 3-deoxy-7-phosphoheptulonate synthase gene.

The O-methyltransferase gene includes an O-methyltransferase gene comt from *Arabidopsis thaliana* (Mouseear cress), an O-methyltransferase gene comt from *Coffea canephora* (*Robusta* coffee), an O-methyltransferase gene comt from *Homo sapiens* (Human), an O-methyltransferase gene comt from *Rattus norvegicus* (rat), an O-methyltransferase gene comt from *Mus musculus* (mouse), and an optional O-methyltransferase gene comt.

The carboxylic acid reductase gene includes a carboxylic acid reductase gene car from *Nocardia* iowensis and a carboxylic acid reductase gene car from *Mycobacterium marinum*.

The 4'-phosphopantetheinyl transferase gene includes a 4'-phosphopantetheinyl transferase gene sfp from *Nocardia* iowensis, a 4'-phosphopantetheinyl transferase gene sfp from *Mycobacterium marinum*, and a 4'-phosphopantetheinyl transferase gene sfp from *Bacillus subtilis*.

The 5-methyltetrahydropteroyltriglutamate-homocysteine methyltransferase gene includes an endogenous *Corynebacterium glutamicum* 5-methyltetrahydropteroyltriglutamate-homocysteine methyltransferase gene metE, and an optional exogenous 5-methyltetrahydropteroyltriglutamate-homocysteine methyltransferase gene.

The S-adenosylmethionine synthase gene includes an endogenous *Corynebacterium glutamicum* S-adenosylmethionine synthase gene metK and an optional exogenous S-adenosylmethionine synthase gene.

The homoserine O-acetyltransferase gene includes an endogenous *Corynebacterium glutamicum* homoserine O-acetyltransferase gene metX and an optional exogenous homoserine O-acetyltransferase gene.

The adenosylhomocysteinase gene includes an endogenous *Corynebacterium glutamicum* adenosylhomocysteinase gene ahcY and an optional exogenous adenosylhomocysteinase gene.

The nucleotide sequence of the endogenous *Corynebacterium glutamicum* transketolase gene tktA is as shown by SEQ ID NO. 83.

The nucleotide sequence of the endogenous *Corynebacterium glutamicum* 3-deoxy-7-phosphoheptulonate synthase gene aroG is as shown by SEQ ID NO. 84.

The nucleotide sequence of the O-methyltransferase gene comt from *Arabidopsis thaliana* is as shown by SEQ ID NO. 85; the nucleotide sequence of the O-methyltransferase gene comt from *Coffea canephora* is as shown by SEQ ID NO. 122; the nucleotide sequence of the O-methyltransferase gene comt from *Homo sapiens* is as shown by SEQ ID NO. 105; the nucleotide sequence of the O-methyltransferase gene comt from *Rattus norvegicus* is as shown by SEQ ID NO. 46; and the nucleotide sequence of the O-methyltransferase gene comt from *Mus musculus* is as shown by SEQ ID NO. 137.

The nucleotide sequence of the carboxylic acid reductase gene car from *Nocardia* iowensis is as shown by SEQ ID NO. 47; and the nucleotide sequence of the carboxylic acid reductase gene car from *Mycobacterium marinum* is as shown by SEQ ID NO. 86.

The nucleotide sequence of the 4'-phosphopantetheinyl transferase gene sfp from *Nocardia* iowensis is as shown by SEQ ID NO. 87; and the nucleotide sequence of the 4'-phosphopantetheinyl transferase gene sfp from *Mycobacterium marinum* is as shown by SEQ ID NO. 48; and the nucleotide sequence of the 4'-phosphopantetheinyl transferase gene sfp from *Bacillus subtilis* is as shown by SEQ ID NO. 106.

The nucleotide sequence of the endogenous *Corynebacterium glutamicum* 5-methyltetrahydropteroyltriglutamate-homocysteine methyltransferase gene metE is as shown by SEQ ID NO. 49.

The nucleotide sequence of the endogenous *Corynebacterium glutamicum* S-adenosylmethionine synthase gene metK is as shown by SEQ ID NO. 50.

The nucleotide sequence of the endogenous *Corynebacterium glutamicum* homoserine O-acetyltransferase gene metX is as shown by SEQ ID NO. 51.

The nucleotide sequence of the endogenous *Corynebacterium glutamicum* adenosylhomocysteinase gene ahcY is as shown by SEQ ID NO. 52.

Further, the exogenous transketolase gene is derived from *Escherichia coli* K12 (tktA, Gene ID: 947420), *Saccharomyces cerevisiae* S288C (tkl1, Gene ID: 856188) or *Bacillus subtilis* 168 (tktA, Gene ID: 937377).

The exogenous 3-deoxy-7-phosphoheptulonate synthase gene is derived from *Escherichia coli* K12 (the nucleotide sequence is as shown by SEQ ID NO. 45), *Saccharomyces cerevisiae* S288C (aro4, Gene ID: 852551) or *Bacillus subtilis* 168 (aroX, Gene ID: 937853).

The exogenous 5-methyltetrahydropteroyltriglutamate-homocysteine methyltransferase gene is derived from

*Escherichia coli* K12 (metE, Gene ID: 948323), *Saccharomyces cerevisiae* S288C (met6, Gene ID: 856825) or *Bacillus subtilis* 168 (metE, Gene ID: 936480).

The exogenous S-adenosylmethionine synthase gene is derived from *Escherichia coli* K12 (metK, Gene ID: 945389), *Saccharomyces cerevisiae* S288C (SAM2, Gene ID: 852113) or *Bacillus subtilis* 168 (metK, Gene ID: 937090).

The exogenous homoserine O-acetyltransferase gene is derived from *Saccharomyces cerevisiae* S288C (met2, Gene ID: 855444) or *Bacillus subtilis* 168 (metAA, Gene ID: 939083).

Preferably, the exogenous transketolase gene is derived from *Escherichia coli* K12.

The exogenous 3-deoxy-7-phosphoheptulonate synthase gene is derived from *Escherichia coli* K12.

The O-methyltransferase gene is derived from *Rattus norvegicus.*

The carboxylic acid reductase gene is derived from *Nocardia* iowensis.

The 4'-phosphopantetheinyl transferase gene is derived from *Mycobacterium marinum.*

The 5-methyltetrahydropteroyltriglutamate-homocysteine methyltransferase gene is derived from endogenous *Corynebacterium glutamicum.*

The S-adenosylmethionine synthase gene is derived from the endogenous *Corynebacterium glutamicum.*

The homoserine O-acetyltransferase gene is derived from the endogenous *Corynebacterium glutamicum.*

The adenosylhomocysteinase gene is derived from the endogenous *Corynebacterium glutamicum.*

Further, a method for constructing a genetically engineered bacterium using glucose as a substrate for de novo synthesis of vanillin includes the following steps:

(1) using *Corynebacterium glutamicum* as an original strain to knock out pcaHG, van, vdh and fud genes, and obtaining modified *Corynebacterium glutamicum;*

(2) expressing the vanillin synthesis module and the methyl cyclic regeneration module in the modified *Corynebacterium glutamicum.*

Another purpose of the present invention is to provide an application of the genetically engineered bacterium for synthesizing vanillin in synthesis of vanillin.

Specifically, the present invention provides an application of the genetically engineered bacterium or the method in producing vanillin.

Specifically, the present invention provides an application of the genetically engineered bacterium or the method in increasing a yield of vanillin.

Specifically, a method for producing the vanillin uses the genetically engineered bacterium or the genetically engineered bacterium constructed by the method for fermentation.

Therefore, the present invention provides a pathway for biosynthesis of vanillin (FIG. 1), which includes:

(1) glucose generates phosphoenolpyruvate (PEP) under the action of a glycolytic pathway of microorganisms, and generates erythrose 4-phosphate (E4P) under the action of a pentose phosphate pathway of microorganisms;

(2) transketolase tktA catalyzes reversible transfer of dicarbonyl groups from 7-heptose phosphate to glyceraldehyde 3-phosphate to generate 5-phosphoxylose and ribose 5-phosphate;

(3) the phosphoenolpyruvate (PEP) and the erythrose 4-phosphate (E4P) are catalyzed by 3-deoxy-D-arabinoheptulose-7-phosphate synthase aroG to generate 3-deoxy-D-arabinoheptulose-7-phosphate (DAHP);

(4) *Corynebacterium glutamicum* generates protocatechuic acid (PCA) in a pathway of own shikimic acid;

(5) the protocatechuic acid (PCA) is catalyzed by O-methyltransferase comt to generate vanillic acid;

(6) the vanillic acid is catalyzed by carboxylic acid reductase car to generate vanillin;

(7) the carboxylic acid reductase car is transformed into a whole enzyme by post-translational modification of catalytic phosphorylation of 4'-phosphopantetheinyl transferase sfp;

the above is the vanillin synthesis module.

(8) strain endogenously generates homoserine;

(9) homoserine O-acetyltransferase metX transfers an acetyl group from coenzyme A to 1-homoserine to form O-acetyl-1-homoserine;

(10) the strain transforms O-acetyl-1-homoserine to L-homocysteine;

(11) the 5-methyltetrahydropteroyltriglutamate-homocysteine methyltransferase metE catalyzes the transfer of a methyl group from 5-methyltetrahydrofolate to homocysteine to form methionine;

(12) the L-methionine is catalyzed by S-adenosylmethionine synthase metK to generate S-adenosyl-L-methionine (SAM);

(13) the S-adenosyl-L-methionine is catalyzed by O-methyltransferase comt to provide a methyl group for protocatechuic acid to generate S-adenosyl-L-homocystein (SAH) and vanillic acid;

(14) the S-adenosyl-L-homocystein is catalyzed by adenosylhomocysteinase ahcY to generate adenosine and L-homocysteine;

the above is the methyl cyclic regeneration module.

Modification of chassis microorganisms: *Corynebacterium glutamicum* is used as an original strain to knock out pcaHG, van, vdh and fud genes with specific steps as follows:

pcaHIG is a protocatechuate 3,4-dioxygenase subunit; the *Corynebacterium glutamicum* has a pathway of β-ketoadipic acid, and uses several aromatic compounds such as PCA as an exclusive source of carbon and energy; the degradation of protocatechuic acid is initiated by protocatechuate 3,4-dioxygenase (PcaGH), which consists of two subunits coded by pcaG and pcaH located in a pcaHGBC operon; and knocking out pcaHG can prevent the consumption of the protocatechuic acid β-ketoadipic acid pathway.

Van is vanillic demethylase and contains vanillic demethylase subunit ABK, which can catalyze the transformation of vanillic acid to protocatechuic acid; and knocking out van can prevent demethylation from vanillic acid to protocatechuic acid, thereby promoting the utilization of the protocatechuic acid.

vdh catalyzes the oxidation of vanillin to generate vanillic acid, which has an obvious oxidation effect on 3,4-dihydroxybenzaldehyde (protocatechuic aldehyde) and 4-hydroxybenzaldehyde, and also has activities of NAD+ and NADP+. Due to the toxicity of vanillin for cells, vdh catalyzes the transformation of vanillin to vanillic acid; and knocking out vdh can reduce the oxidation of vanillin and increase the accumulation of vanillin.

Fud is an alcoholdehydrogenase, which uses NADPH (not NADH) as a cofactor to transform vanillin into vanillyl alcohol; and knocking out Fud can significantly reduce the process of reducing vanillin to vanillyl alcohol.

It may be seen from the above technical solution that compared with the prior art, the present invention discloses the genetically engineered bacterium using the glucose as the substrate for de novo synthesis of vanillin and the application thereof, which modifies the *Corynebacterium glutamicum* in three aspects, including construction and enhancement of a vanillin synthesis pathway (involving tktA, aroG, comt and car), enhancement of a methyl regeneration system (involving metE, metK, metX, and ahcY), knocking out of a vanillin catabolism pathway and a byproduct metabolism pathway (involving pcaHG, van, vdh and fud); and finally a recombinant *Corynebacterium glutamicum* for efficiently synthesizing the vanillin is constructed.

The host *Corynebacterium glutamicum* used in the present invention is a food-grade microorganism, which has no pathogenicity to humans and animals, has better growth advantages under the same culture conditions, and can accumulate higher concentration of vanillin than other strains. Repeated experiments show that the highest concentration of vanillin produced by the shaking flask fermentation of recombinant *Corynebacterium glutamicum* can reach 765.85 mg/L, which is the highest yield of vanillin of de novo biosynthesis in the reported related research at present, and has great industrial application prospects in the biological production of vanillin with high yield.

The genetically engineered bacterium constructed by the present invention is safe and non-toxic, can use the microbiological fermentation method to produce the vanillin with the glucose as the substrate, and is simple in culture medium components, stable in batches, and low in production cost.

DESCRIPTION OF DRAWINGS

To more clearly describe the technical solutions in the embodiments of the present invention or in the prior art, the drawings required to be used in the description of the embodiments or the prior art will be simply presented below. Apparently, the drawings in the following description are merely embodiments of the present invention, and for those ordinary skilled in the art, other drawings can also be obtained according to the provided drawings without contributing creative labor.

DETAILED DESCRIPTION

Figure 1:
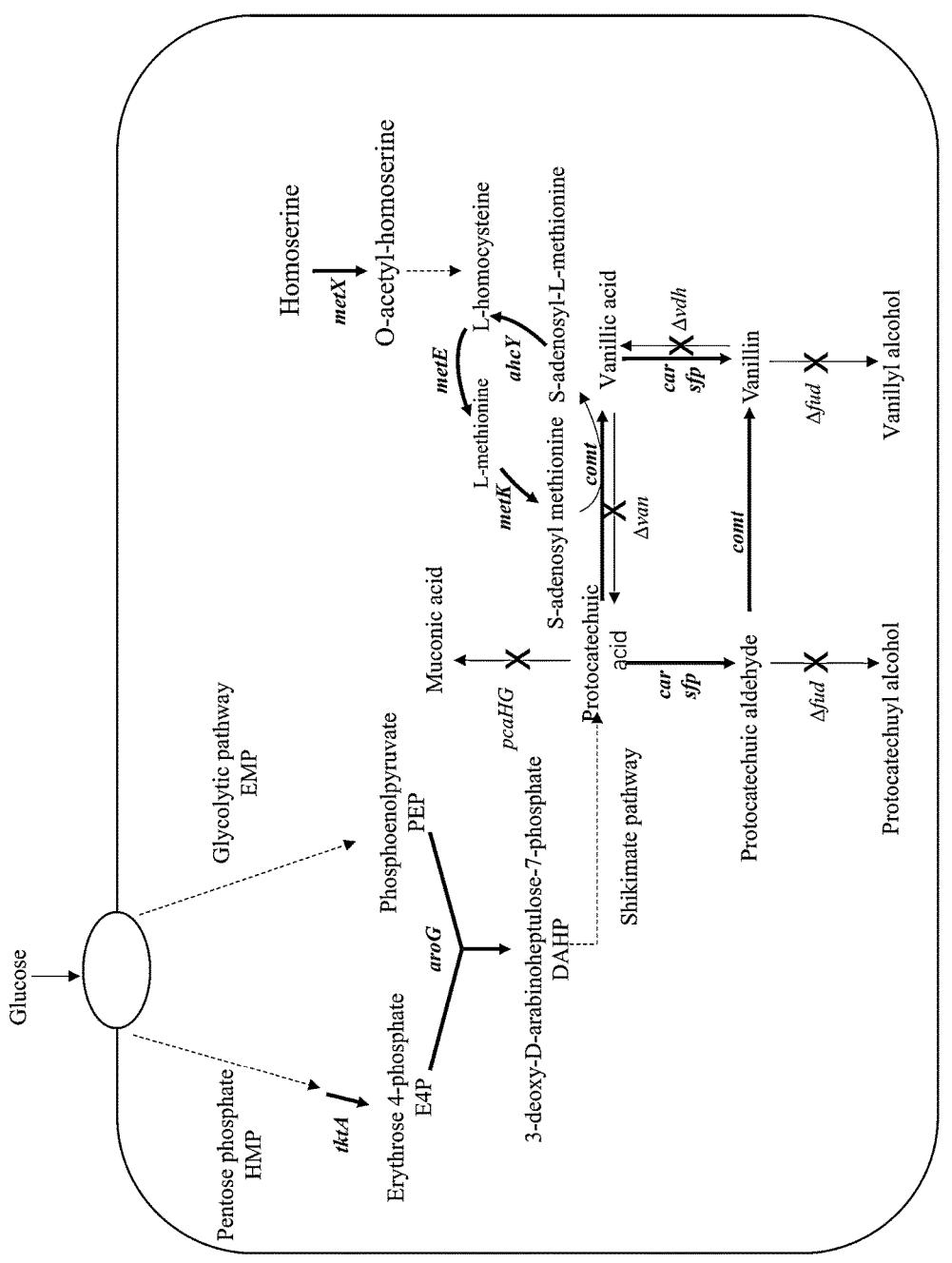
FIG. 1 is a pathway of biological synthesis of vanillin according to the present invention.

Technical solutions in the embodiments of the present invention are described clearly and fully below in combination with the drawings in the embodiments of the present invention. Apparently, the described embodiments are merely part of the embodiments of the present invention, not all of the embodiments. Based on the embodiments in the present invention, all other embodiments obtained by those ordinary skilled in the art without contributing creative labor will belong to the protection scope of the present invention.

LBHIS liquid culture medium: peptone 5.0 g/L, yeast powder 2.5 g/L, NaCL 5.0 g/L, brain heart infusion (BHI) 18.5 g/L, and sorbitol 91.0 g/L. 1.8%-2% of agar is added to the corresponding LBHIS solid culture medium is added with The LBHIS culture medium is mainly used for culturing *Corynebacterium glutamicum* in a test tube and a solid plate.

EPO liquid culture medium: peptone 10.0 g/L, yeast powder 5.0 g/L, NaCL 10.0 g/L, glycine 30.0 g/L, and Tween80 10.0 g/L. The EPO culture medium is mainly used for preparing *Corynebacterium glutamicum* competent cells.

30% sucrose culture medium: peptone 10.0 g/L, yeast powder 5.0 g/L, NaCL 10.0 g/L, and sucrose 300.0 g/L.

20% sucrose solid culture medium: peptone 10.0 g/L, yeast powder 5.0 g/L, NaCL 10.0 g/L, sucrose 200.0 g/L, and agar 15.0 g/L. LB-suc culture medium (30% sucrose culture medium, and 20% sucrose solid culture medium) is mainly used for homologous recombination and screening in a *Corynebacterium glutamicum* gene knockout experiment.

LBG culture medium: peptone 10.0 g/L, yeast powder 5.0 g/L, NaCL 10.0 g/L and glucose 20.0 g/L. The LBG culture medium is mainly used as a seed culture medium in fermentation of *Corynebacterium glutamicum*.

Fermentation culture medium: glucose 65.0 g/L, urea 5.0 g/L, maize extract powder 8.0 g/L, biotin $4\times10^{-4}$ g/L, $VB_1$ biotin $4\times10^{-4}$ g/L, $K_2HPO_4$ 1.0 g/L, $KH_2PO_4$ 1.0 g/L, $CaCl_2\cdot2H_2O$ 29.4 mg/L, $MgSO_4\cdot7H_2O$ 1.2325 g/L, and trace element solution 0.2%. (A preparation method of the trace element solution: measuring 1 g of $FeSO_4\cdot7H_2O$, 1 g of $MnSO_4\cdot H_2O$, 0.1 g of $ZnSO_4\cdot7H_2O$, 0.2 g of $CuSO_4$, and 0.002 g of $NiCl_2\cdot6H_2O$, adding water to fix the volume at 100 mL, adding 100 μl of concentrated hydrochloric acid to adjust pH, then filtering bacteria, and adding 0.2% in a fermentation culture medium system). The fermentation culture medium is mainly used for the shake-flask fermentation of *Corynebacterium glutamicum*.

Embodiment 1

A method for constructing a genetically engineered bacterium using glucose as a substrate for de novo synthesis of vanillin includes the following steps:

With genome DNA of *Corynebacterium glutamicum* ATCC13032 as a template, pcaHG-L (as shown by SEQ ID NO. 1) is amplified with primers pcaHG-L-up/pcaHG-L-down, and pcaHG-R (as shown by SEQ ID NO. 2) is amplified with primers pcaHG-R-up/pcaHG-R-down to obtain an upstream and a downstream homologous arms with all pcaHG deleted. The primer sequences are as follows:

pcaHG-L-up:

SEQ ID NO. 3

5'-ATGATTACGCCATCGCATTGCCGAAAAGC-3';;

pcaHG-L-down:

SEQ ID NO. 4

5'-GGTCAATGCGAGACCTTTCTGCGTC-3';;

-continued

```
pcaHG-R-up:
                                      SEQ ID NO. 5
5'-AAAGGTCTCGCATTGACCCGATCTTTATACTCCGAC-3';;

pcaHG-R-down:
                                      SEQ ID NO. 6
5'-CTCAACGTTGACGGTGATGCCA-3';.
```

Gene amplification system: 25 μL of Primestar (Takara), 2 μL of each of upstream and downstream primers, 1 μL of template, and 20 μL of ddH₂O.

Gene amplification procedure: predegenation at 98° C. for 3 min; degeneration at 98° C. for 10 se; annealing at 55° C. for 30 s; extension 10 s/kb for 35 cycles at 72° C.; and extension at 72° C. for 10 min.

PCR products are subjected to agarose gel electrophoresis and product recovery to obtain gene fragments pcaHG-L and pcaHG-R.

Plasmid vector pk18mobsacb is linearized with the primers pk-pcaHG-F and pk-pcaHG-R to obtain a pk-pcaHIG vector, and the primer sequences are as follows:

```
pk-pcaHG-F:
                                      SEQ ID NO. 7
5'-ATCACCGTCAACGTTGAGCTCGGTAGATCCTCTAGAGT-3';;

pk-pcaHG-R:
                                      SEQ ID NO. 8
5'-AATGCGATGGCGTAATCATGTCATAGCTGTTTCCTG-3';.
```

3 μL of pcaHIG-L vector, 3 μL of pcaHG-R vector, 4 μL of pk-pcaHG vector and 10.0 μl of Gibson ligase are added into a PCR tube, wherein the ligation temperature is 50° C., the ligation time is 15 min, and the total system is 20 μL.

20 μl of total ligation system of Gibson ligation is transformed to *E. coli* Trans10 commercial competence (TransGen Biotech) for culture and preservation. The transformation operation is strictly carried out according to instructions; after cultured at 37° C. for 1 h, the whole system is coated on an LB plate (containing 50 μg/mL kanamycin), then the whole system is cultured at 37° C. for 12 h, and about 10 to 20 single colonies are selected for colony PCR amplification and DNA sequencing verification. Primers for colony PCR amplification and DNA sequencing are as follows:

```
Pklj-F:
                                      SEQ ID NO. 9
5'-GCGGATAACAATTTCACACAGGA-3';;

Pklj-R:
                                      SEQ ID NO. 10
5'-cgggcctcttcgctattac-3';.
```

A correct single colony is selected, and named *Escherichia coli* WJ001; and after propagation and plasmid extraction, WJ001 plasmid is obtained. The *Escherichia coli* WJ001 plasmid is electrotransformed into competence of *Corynebacterium glutamicum* ATCC13032.

Competence cells of *Corynebacterium glutamicum* ATCC13032 are prepared as follows: glycerol preserved strains of *Corynebacterium glutamicum* ATCC13032 are selected, streaked and inoculated onto an LBHIS plate and cultured for about 24-30 h in an incubator at 30° C.; colonies are selected from the plate and inoculated into a test tube with LBHIS liquid culture medium to be cultured for 12 h, and inoculated into 20 ml EPO culture medium at a certain inoculation amount, so that an initial OD₆₀₀ is about 0.3, the colonies are subjected to shake-flask culture for about 3-5 h at 30° C., and when OD₆₀₀ reaches about 0.9, bacterial solution is collected and placed into a centrifugal tube, and subjected to ice-bath for 15 min to cool the bacteria cells to 0° C.; after frozen centrifuging for 10 min at 4500 rpm and 4° C., the bacterial cells are collected (split charged in 1.5 mL centrifugal tubes), supernatant is removed, and the bacterial cells are re-suspended with 100 μL of pre-cooled 10% sterile glycerol (three tubes of bacterial cells are mixed into one); the previous step is repeated three times; after washing, the bacterial cells are re-suspended by 100 μL of sterile glycerol, and then split charged and directly used for electrotransformation.

The electrotransformation method is as follows: 2-4 μL of plasmid is added into each tube of competent cells, uniformly mixed and ice-bathed for 5-10 min; and the mixed solution is transferred into a pre-cooled 0.2 cm electric shock cup for electric shock for 5 ms with 1.8 kv, 50 μF and 100Ω. After the electric shock, the mixed solution is immediately added to 800 μL LBHIS liquid culture medium and slightly mixed, then the mixed solution is sucked into a 1.5 mL centrifugal tube for water bath or metal bath for 6 min at 46° C., and then cultured at 30° C. for 2-3 h; and the mixed solution is centrifuged for 1.5 min at 8000 rpm, supernatant is removed, and about 100-200 μl of bacterial solution is preserved and uniformly mixed and coated on a LBHIS solid culture medium plate containing 50 μg/mL kanamycin and cultured at 30° C. for 24-36 h.

The single colony growing on the plate is selected to verify a sacB gene, and only the colony that can grow on a Kana-resistant plate and also can amplify sacB gene (a band size is 999 bp) is the strain with the first homologous recombination. The verification primers are as follows:

```
sac-F:
                                      SEQ ID NO. 11
5'-CCCATATTACACGCCATGATATGCT-3';;

sac-R:
                                      SEQ ID NO. 12
5'-GCATGTAAATATCGTTAGACGTAATGCCG-3';.
```

The strain that is verified to be correct is selected and inoculated into 30% sucrose culture medium to be cultured for 24 h, and after the bacterial solution is turbid, the bacterial solution is streaked on the 20% sucrose solid culture medium; the single colony on the plate is selected for colony PCR of sacB genes; and the single colonies that do not amplify the sacB genes are subjected to secondary colony PCR with verification primers, and the pcaHG verification (the band size is 3376 bp) primers are as follows:

```
pcaHG-verification-F:
                                      SEQ ID NO. 13
5'-CGCGACTTGCCATCACATC-3';;

pcaHG-verification-R:
                                      SEQ ID NO. 14
5'-GTCAAGCAGGCTAAACCGGAG-3';.
```

According to the knock-out principle of *Corynebacterium glutamicum*, after the second homologous recombination, the whole knock-out plasmid may fall off from the genome, so as to achieve the purpose of knock-out, so that the colony with the second recombination may no longer contain sacB genes; the bacteria that is verified by the verification primers to succeed in knock-out are inoculated in the LBHIS liquid medium for culture, and then streaked on the LBHIS solid medium plate for purification and re-verification; and after confirmation, the bacteria can be preserved for use, and cgATCC13032ΔpcaHG is named *Corynebacterium glutamicum* CG001.

(2) With genome DNA of *Corynebacterium glutamicum* ATCC13032 as a template, van-L (as shown by SEQ ID NO. 15) is amplified with primers van-L-up/van-L-down, and van-R (as shown by SEQ ID NO. 16) is amplified with primers van-R-up/van-R-down to obtain an upstream and a downstream homologous arms with all van deleted. The primer sequences are as follows:

```
van-L-up:
                                SEQ ID NO. 17
5'-AACAGCTATGACATGATTACGATAAGCTGCTCATGCTTGGC-3';;

van-L-down:
                                SEQ ID NO. 18
5'-CTGATATCTCGACATTGCTGAGTTAATGTCAGCTGGGGTC
TC-3';;

van-R-up:
                                SEQ ID NO. 19
5'-CAGCAATGTCGAGATATCAGTGG-3';;

van-R-down:
                                SEQ ID NO. 20
5'-AGAGGATCTACCGAGCTCTCATCAGTGTGTTTCGGGAGC-3';.
```

The plasmid vector PK-JL is linearized with the primers pk-van-F and pk-van-R to obtain a pk-van vector, and the primer sequences are as follows:

```
    pk-van-F:
                                SEQ ID NO. 21
    5'-GAGCTCGGTAGATCCTCTAGAGT-3';;

pk-van-R:
                                SEQ ID NO. 22
    5'-CGTAATCATGTCATAGCTGTTTCCTG-3';.
```

The gene amplification system and the gene amplification procedure are the same as above, and van-L, van-R and pk-van vectors are obtained; the verification method of ligation and transformation is the same as above, and *Escherichia coli* WJ002 is obtained; and after propagation and plasmid extraction, WJ002 plasmid is obtained.

The *Escherichia coli* WJ002 plasmid is electrotransformed into competence of *Corynebacterium glutamicum* CG001. The competence preparation, electrotransformation, sacB verification, and culture with sucrose culture medium are the same as above, and the partial deletion van verification (the size band is 4459 bp) primers are as follows:

```
    van-verification-F:
                                SEQ ID NO. 23
    5'-TTGATGGTGTCCGCAAAATCG-3';;

van-verification-R:
                                SEQ ID NO. 24
    5'-ACCGACACGACCCATACCAA-3';.
```

The bacteria that are verified with the verification primers to succeed in knock-out are inoculated in LBHIS liquid medium for culture, and then streaked on LBHIS solid medium plate for purification and re-verification; and after confirmation, the bacteria can be preserved for use, and cgATCC13032ΔpcaHIGΔvan is named *Corynebacterium glutamicum* CG002.

(3) With genome DNA of *Corynebacterium glutamicum* ATCC13032 as a template, vdh-L (as shown by SEQ ID NO. 25) is amplified with primers vdh-L-up/vdh-L-down, and vdh-R (as shown by SEQ ID NO. 26) is amplified with primers vdh-R-up/vdh-R-down to obtain an upstream and a downstream homologous arms with all vdh deleted. The primer sequences are as follows:

```
vdh-L-up:
                                SEQ ID NO. 27
5'-AACAGCTATGACATGATTACGCGACGGTATTCCTGCAGATG
A-3';;

vdh-L-down:
                                SEQ ID NO. 28
5'-CTTTAGGAGACCTTCGCTAATCCGCTGAACAGG-3';;

vdh-R-up:
                                SEQ ID NO. 29
5'-GATTAGCGAAGGTCTCCTAAAGTTGATTGTGGATAC-3';;

vdh-R-down:
                                SEQ ID NO. 30
5'-AGCTCAGTATGGGAAGCATTGCTTGC-3';.
```

The plasmid vector PK-JL is linearized with primers pk-vdh-F and pk-vdh-R to obtain a pk-vdh vector, and the primer sequences are as follows:

```
pk-vdh-F:
                                SEQ ID NO. 31
5'-AATGCTTCCCATACTGAGCTCGGTAGATCCTCTAGAGT-3';;

pk-vdh-R:
                                SEQ ID NO. 32
5'-CGTAATCATGTCATAGCTGTTTCCTG-3';.
```

The gene amplification system and the gene amplification procedure are the same as above, and vdh-L, vdh-R and pk-vdh vectors are obtained; the verification method of ligation and transformation is the same as above, and *Escherichia coli* WJ003 is obtained; and after propagation and plasmid extraction, WJ003 plasmid is obtained.

The *Escherichia coli* WJ003 plasmid is electrotransformed into competence of *Corynebacterium glutamicum* CG002. The competence preparation, electrotransformation, sacB verification, and culture with sucrose culture medium are the same as above, and the vdh verification (the size band is 3653 bp) primers are as follows:

```
    vdh-verification-F:
                                SEQ ID NO. 33
    5'-GTGAATCAATCATTGCTGATTACCTTGTC-3';;

vdh-verification-R:
                                SEQ ID NO. 34
    5'-CTTATGCCTTTGCGTAATGTTGATAGAAC-3';.
```

The bacteria that are verified with the verification primers to succeed in knock-out are inoculated in LBHIS liquid medium for culture, and then streaked on LBHIS solid medium plate for purification and re-verification; and after confirmation, the bacteria can be preserved for use, and cgATCC13032ΔpcaHIGΔvanΔvdh is named *Corynebacterium glutamicum* CG003.

(4) With genome DNA of *Corynebacterium glutamicum* ATCC13032 as a template, fud-L (as shown by SEQ ID NO. 35) is amplified with primers fud-L-up/fud-L-down, and fud-R (as shown by SEQ ID NO. 36) is amplified with primers fud-R-up/fud-R-down to obtain an upstream and a downstream homologous arms of fud. The primer sequences are as follows:

```
fud-L-up:
                                    SEQ ID NO. 37
5'-TTACGAATTCGAGCTCGGTAAAGCCACCGGATTTAGCGC-3';;

fud-L-down:
                                    SEQ ID NO. 38
5'-CCCAGTTAGCCTACCGAAAAATCAA-3';;

fud-R-up:
                                    SEQ ID NO. 39
5'-TTCGGTAGGCTAACTGGGCCCTGGCTTTGGAGAGTTACT-3';;

fud-R-down:
                                    SEQ ID NO. 40
5'-TCGACTCTAGAACACGATTCTCAAGCTTACTGCG-3';.
```

The plasmid vector PK-JL is linearized with primers pk-fud-F and pk-fud-R to obtain a pk-fud vector, and the primer sequences are as follows:

```
    pk-fud-F:
                                    SEQ ID NO. 41
    5'-AGAATCGTGTTCTAGAGTCGACCTGCAGGC-3';;

pk-fud-R:
                                    SEQ ID NO. 42
    5'-TTTACCGAGCTCGAATTCGTAATCATGT-3';.
```

The gene amplification system and the gene amplification procedure are the same as above, and fud-L, fud-R and pk-fud vectors are obtained; the verification method of ligation and transformation is the same as above, and *Escherichia coli* WJ004 is obtained; and after propagation and plasmid extraction, WJ004 plasmid is obtained.

The *Escherichia coli* WJ004 plasmid is electrotransformed into competence of *Corynebacterium glutamicum* CG003. The competence preparation, electrotransformation, sacB verification, and culture with sucrose culture medium are the same as above, and the fud verification (the size band is 3431 bp) primers are as follows:

```
    fud-verification-F:
                                    SEQ ID NO. 43
    5'-CTTTCTTGGGAAAGGCCCG-3';;

fud-verification-R:
                                    SEQ ID NO. 44
    5'-TGGCACCTACAACCTCACCAA-3';.
```

The bacteria that are verified with verification primers to succeed in knock-out are inoculated in LBHIS liquid medium for culture, and then streaked on LBHIS solid medium plate for purification and re-verification; and after confirmation, the bacteria can be preserved for use, and cgATCC13032ΔpcaHIGΔvanΔvdhΔfud is named *Corynebacterium glutamicum* CG004.

(5) With genome DNA of *Escherichia coli* k12 as a template, a fragment tktA (Gene ID: 947420) is amplified with primers tktA-up/tktA-down to obtain the tktA fragment derived from *Escherichia coli* with a seamless coloning homologous arm and a ribosome bind site (RBS) ligated with aroG.

A base A on a 436$^{th}$ site of an aroG gene sequence derived from *Escherichia coli* k12 is mutated to a base G, and a feedback-resistant suppressor gene sequence (as shown by SEQ ID NO. 45) is obtained; and with feedback-resistant suppressor gene sequence as a template, the fragment aroG is amplified with primers aroG-up/aroG-down to obtain an aroG fragment derived from the *Escherichia coli* with a seamless coloning homologous arm and RBS ligated with plasmid.

With a codon-optimized comt fragment (as shown by SEQ ID NO. 46) of *Rattus norvegicus* synthesized by Beijing Genomics Institute as a template, the fragment comt is amplified with primers comt-up/comt-down to obtain the comt fragment derived from *Rattus norvegicus* with a seamless coloning homologous arm and RBS ligated with tktA.

With a codon-optimized car gene fragment of *Nocardia iowensis* synthesized by Beijing Genomics Institute (as shown by SEQ ID NO. 47) as a template, the fragment car is amplified with primers car-up/car-down to obtain the car fragment derived from *Nocardia* iowensis with a seamless coloning homologous arm and RBS ligated with metX.

With a codon-optimized sfp fragment (as shown by SEQ ID NO. 48) of *Mycobacterium marinum* synthesized by Beijing Genomics Institute as a template, the fragment sfp is amplified with primers sfp-up/sfp-down to obtain the sfp fragment derived from *Mycobacterium marinum* with a seamless coloning homologous arm and RBS ligated with car and plasmid.

With the genome DNA of *Corynebacterium glutamicum* ATCC13032 as a template, the fragment metE (as shown by SEQ ID NO. 49) is amplified with primers metE-up/metE-down to obtain a metE fragment derived from *Corynebacterium glutamicum* with a seamless coloning homologous arm and RBS ligated with ahcY and plasmid.

With the genome DNA of *Corynebacterium glutamicum* ATCC13032 as a template, the fragment metK (as shown by SEQ ID NO. 50) is amplified with primers metK-up/metK-down to obtain a metK fragment derived from *Corynebacterium glutamicum* with a seamless coloning homologous arm and RBS ligated with plasmid.

With the genome DNA of *Corynebacterium glutamicum* ATCC13032 as a template, the fragment metX (as shown by SEQ ID NO. 51) is amplified with primers metX-up/metX-down to obtain a metX fragment derived from *Corynebacterium glutamicum* with a seamless coloning homologous arm and RBS ligated with metK.

With the genome DNA of *Corynebacterium glutamicum* ATCC13032 as a template, the fragment ahcY (as shown by SEQ ID NO. 52) is amplified with primers ahcY-up/ahcY-down to obtain an ahcY fragment derived from *Corynebacterium glutamicum* with a seamless coloning homologous arm and RBS ligated with comt.

The primer sequences are as follows:

```
tktA-up:
                                    SEQ ID NO. 53
5'-TAAAAGCGCGTCGCGGGTAAAAGGAGGATATACATATGTCCT
CACGTAAAGAGCTTGC-3';;

tktA-down:
                                    SEQ ID NO. 54
5'-TTACAGCAGTTCTTTTGCTTTCGC-3';;

aroG-up:
                                    SEQ ID NO. 55
5'-GGAAACAGACCATGGAATTCAAGGAGGATATACATATGAATT
ATCAGAACGACGATTTACGC-3';;

aroG-down:
                                    SEQ ID NO. 56
5'-TTACCCGCGACGCGCTTTTA-3';;

comt-up:
                                    SEQ ID NO. 57
5'-AAAGCAAAAGAACTGCTGTAAAAGGAGGATATACATATGGG
TGATACCAAAGAACAGCG-3';;
```

-continued

```
comt-down:
                                    SEQ ID NO. 58
5'-TTAAGATTTATCAGGGCTACTAGGTCCC-3';;

car-up:
                                    SEQ ID NO. 59
5'-CATCGAGTTCTACATCTAATCTAGAAAGGAGGATATACATATG
GCAGTGGATTCCCCAG-3';;

car-down:
                                    SEQ ID NO. 60
5'-TTACAGCAGCTGCAGCAGTTC-3';;

sfp-up:
                                    SEQ ID NO. 61
5'-AACTGCTGCAGCTGCTGTAAGGATCCCCAAGGAGGATATACAT
ATGACCGTGGGCACTCTG-3';;

sfp-down:
                                    SEQ ID NO. 62
5'-CGCCAAAACAGCCAAGCTGAATTCGAGCTCGGTACCCTTAC
AGCACGATTGCAGTCAG-3';;

metE-up:
                                    SEQ ID NO. 63
5'-CGGAGCACTACCGCTACTAAAAGGAGGATATACATATGACTT
CCAACTTTTCTTCCACTG-3';;

metE-down:
                                    SEQ ID NO. 64
5'-TCTAGAGGATCCCCGGGTACCGAGCTCTTAGATAGTTGCT
CCGATTTTCTCACG-3';;

metK-up:
                                    SEQ ID NO. 65
5'-TTAAGCTTGCATGCCTGCAGGTCGACAAGGAGGATATACATG
TGGCTCAGCCAACCG-3';;

metK-down:
                                    SEQ ID NO. 66
5'-TTAGGCCAACTTGAGGGCTG-3';;

metX-up:
                                    SEQ ID NO. 67
5'-CAGCCCTCAAGTTGGCCTAAAAGGAGGATATACATATGCCC
ACCCTCGCG-3';;

metX-down:
                                    SEQ ID NO. 68
5'-TCTAGATTAGATGTAGAACTCGATGTAGGTCG-3';;

ahcY-up:
                                    SEQ ID NO. 69
5'-CCTAGTAGCCCTGATAAATCTTAAAAGGAGGATATACATATG
GACTTCAAGGTTGCCGA-3';;

ahcY-down:
                                    SEQ ID NO. 70
5'-TTAGTAGCGGTAGTGCTCCG-3';.
```

The gene amplification system and the gene amplification procedure are the same as above.

PCR products are subjected to agarose gel electrophoresis and product recovery to obtain corresponding gene products from different sources, such as tktA, aroG, comt, car, sfp, metE, metK, metX and ahcY.

The plasmid vector pEC-XK99E is linearized with the primers pec-F and pec-R to obtain a pec vector, and the primer sequences are as follows:

```
pec-F:
                                    SEQ ID NO. 71
5'-TACCCGGGGATCCTCTAGAGTC-3';;

pec-R:
                                    SEQ ID NO. 72
5'-GAATTCCATGGTCTGTTTCCTGTG-3';.
```

The amplification system and procedure is the same as the gene amplification system and procedure.

The plasmid vector pXMJ19 is linearized with the primers px-F and px-R to obtain a pxmj vector, and the primer sequences are as follows:

```
px-F:
                                    SEQ ID NO. 73
5'-CGAATTCAGCTTGGCTGTTTTGGCG-3';;

px-R:
                                    SEQ ID NO. 74
5'-TGCAGGCATGCAAGCTTAATTAATT-3';.
```

1.5 μl of tktA vector, 2.5 μl of aroG vector, 1.0 μl of comt vector, 1.5 μl of metE vector, 1.5 μl of ahcY vector, and 2.0 μl of pec vector from different sources, and 10.0 μl of Gibson enzyme are added into a PCR tube.

The ligation temperature is 50° C., the ligation time is 15 min, and a whole system is 20 μL.

20 μl of total ligation system of Gibson ligation is transformed into *E. coli* Trans10 commercial competence for culture and preservation. The transformation operation is strictly carried out according to instructions; after cultured at 37° C. for 1 h, the whole system is coated on an LB plate (containing 50 μg/mL kanamycin), then the whole system is cultured at 37° C. for 12 h, and about 10 to 20 single colonies are selected for colony PCR amplification and DNA sequencing verification. Primers for colony PCR amplification and DNA sequencing are as follows:

```
Pec-F1:
                                    SEQ ID NO. 75
5'-GGCTGTGCAGGTCGTAAATCAC-3';;

Pec-R1:
                                    SEQ ID NO. 76
5'-AGTTCCCTACTCTCGCATGGG-3';.
```

A correct single colony is selected, and named *Escherichia coli* WJ101; and after propagation and plasmid extraction, WJ101 plasmid is obtained.

3.0 μl of car vector, 1.0 μl of sfp vector, 2.0 μl of metK vector, 2.0 μl of metX vector, 2.0 μl of pxmj vector, and 10.0 μl of Gibson enzyme are added into a PCR tube.

The ligation temperature is 50° C., the ligation time is 15 min, and a whole system is 20 μL.

20 μl of total ligation system of Gibson ligation is transformed into *E. coli* Trans10 commercial competence (TransGen Biotech) for culture and reservation. The transformation operation is strictly carried out according to instructions; after cultured at 37° C. for 1 h, the whole system is coated on an LB plate (containing 50 μg/mL kanamycin), then the whole system is cultured at 37° C. for 12 h, and about 10 to 20 single colonies are selected for colony PCR amplification and DNA sequencing verification. Primers for colony PCR amplification and DNA sequencing are as follows:

```
Pxmj-F:
                                    SEQ ID NO. 77
5'-CTGTGGTATGGCTGTGCAGGTC-3';;

Pxmj-R:
                                    SEQ ID NO. 78
5'-ATGCCTGGCAGTTCCCTACT-3';.
```

A correct single colony is selected, and named *Escherichia coli* WJ201; and after propagation and plasmid extraction, WJ201 plasmid is obtained.

2.0 μl of *Escherichia coli* WJ101 plasmid and 2.0 μl of *Escherichia coli* WJ201 plasmid are electrotransformed into competence of *Corynebacterium glutamicum* CG004 at the same time. The competence preparation and electrotransformation are the same as above. The plasmid is uniformly coated on the LBHIS solid culture medium plate containing 50 μg/mL kanamycin and 5 μg/mL chloramphenicol and cultured at 30° C. for 24-36 h.

The single colony growing on the plate is selected to verify kana and cm genes, and only the colony that can grow on a kana and chloramphenicol resistant plate and also can amplify kana and cm genes is a target strain, which is named *Corynebacterium glutamicum* CG101, and the verification primers are as follows:

```
kana-F:
                                        SEQ ID NO. 79
5'-ATGATTGAACAAGATGGATTGCACG-3';;

kana-R:
                                        SEQ ID NO. 80
5'-TCAGAAGAACTCGTCAAGAAGGC-3';;

Cm-R:
                                        SEQ ID NO. 81
5'-CCTGCCACTCATCGCAGTAC-3';;

Cm-F:
                                        SEQ ID NO. 82
5'-ATGGAGAAAAAATCACTGGATATACCACC-3';.
```

The *Corynebacterium glutamicum* CG101, a genetically engineered strain of *Corynebacterium glutamicum*, is subjected to 50 mL system fermentation verification, an LBG culture medium is used for culturing seeds, and fermentation culture medium solution is used for fermentation.

The fermentation of the *Corynebacterium glutamicum* CG101 includes three steps:

Test tube inoculation: 100 μL of *Corynebacterium glutamicum* CG101 that is preserved at the temperature of −80° C. is collected and transferred into a test tube containing 4 mL of LBHIS liquid culture (containing 50 μg/mL kanamycin and 5 μg/mL chloramphenicol) and cultured at 30° C. for 12 h-14 h.

Seed inoculation: the test tube after cultured for 12-14 h is taken out, 1 mL of bacterial solution in the test tube is transferred into the LBG liquid culture medium of a 20 mL system (a 100 mL baffle-free conical bottle is used as a container, which contains 50 μg/mL kanamycin and 5 μg/mL chloramphenicol), and cultivated in a constant temperature shaker at 30° C. and 200 rpm for 12-14 h.

Figure 2:
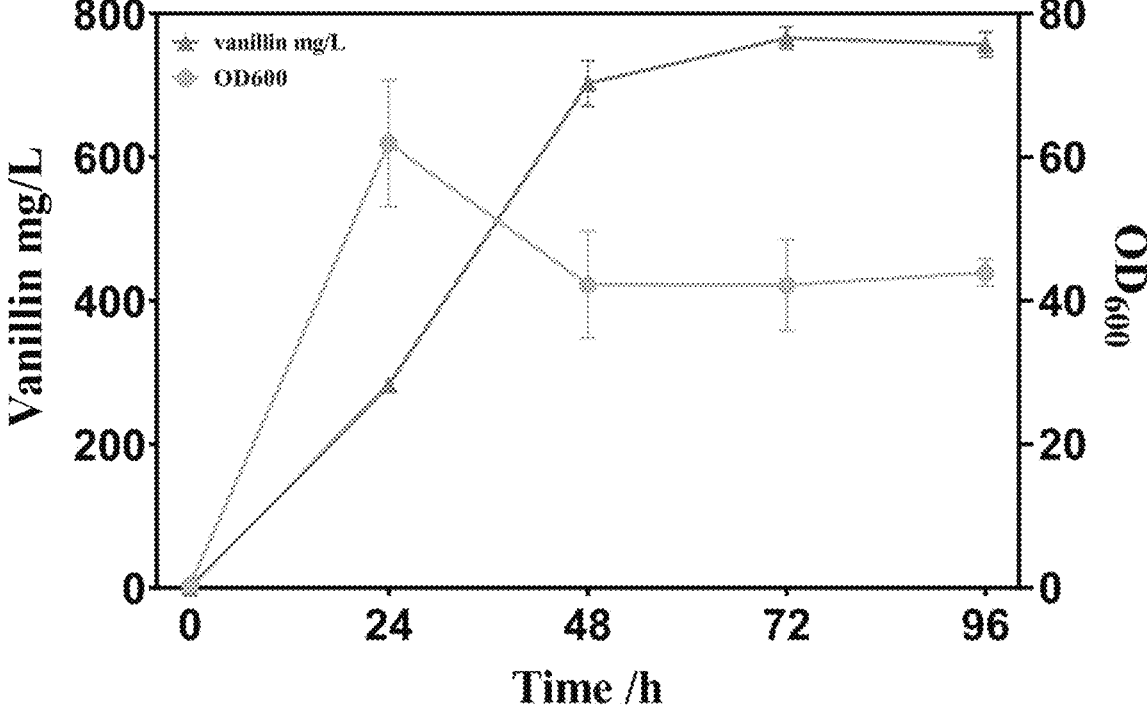
FIG. 2 shows a yield and biomass $OD_{600}$ of vanillin synthesized by genetically engineered bacteria constructed in embodiment 1 of the present invention by shaking flask fermentation with glucose as substrate at different times.

Inoculation of fermentation culture medium: a seed weight inoculated in the fermentation solution of 50 mL system (250 mL conical bottle with a baffle is used as a container, and the fermentation culture medium contains 50 μg/mL kanamycin and 5 μg/mL chloramphenicol) is 5% of the total fermentation system, the pH of the fermentation solution is regulated by strong ammonia water, the fermentation solution is cultured in the constant temperature shaker at 30° C. and 200 rpm for 96 h (0.8 mM IPTG is added for induction after culture for 3 h), every 24 h is a sampling point in the fermentation process, and $OD_{600}$ and a vanillin concentration of a target product are detected. (1) Detection of $OD_{600}$: the fermentation solution is charged into a cuvette, and diluted 50 times with deionized water, and then a light absorption value (600 nm) is measured by an ultraviolet spectrophotometer, and the $OD_{600}$ is determined. (2) Determination of vanillin concentration in the fermentation solution: the vanillin in the fermentation solution is detected by a UltiMate 3000 high performance liquid chromatograph (HPLC, Thermo Fisher Scientific); and the detection method includes: a flow phase includes a phase A (0.1% formic acid aqueous solution) and a phase B (pure methanol); ZORBAX SB-C18 reversed column is used as the chromatographic column, a column temperature is set at 28° C., a flow rate of the flow phase is set at 1.0 mL/min, an ultraviolet detector is used for detection, and an ultraviolet absorption wavelength is set at 260 nm; and finally, contents of products and other metabolites are calculated from data peaks of different fermentation samples according to the standard curves drawn by standard samples. Results are shown in Table 1 and FIG. 2.

TABLE 1

| Time (h) | Vanillin (mg/L) | $OD_{600}$ |
|---|---|---|
| 0 | 0 | 0.464 |
| 24 | 282.53 | 61.9 |
| 48 | 702.82 | 42.3 |
| 72 | 765.85 | 42.2 |
| 96 | 756.87 | 43.9 |

Embodiment 2

A method for constructing a genetically engineered bacterium using glucose as a substrate for de novo synthesis of vanillin includes the following steps:

With the genome DNA of *Corynebacterium glutamicum* ATCC13032 as a template, a fragment tktA (as shown by SEQ ID NO. 83) is amplified with primers tktA-up2/tktA-down2 obtain a tktA fragment derived from *Corynebacterium glutamicum* with a seamless coloning homologous arm and ribosome bind site (RBS) ligated with aroG.

With the genome DNA of *Corynebacterium glutamicum* ATCC13032 as a template, a fragment aroG (as shown by SEQ ID NO. 84) is amplified with primers aroG-up2/aroG-down2 to obtain an aroG fragment derived from *Corynebacterium glutamicum* with a seamless coloning homologous arm and RBS ligated with plasmid.

With a codon-optimized comt fragment (as shown by SEQ ID NO. 85) of *Arabidopsis thaliana* synthesized by Beijing Genomics Institute as a template, the fragment comt is amplified with primers comt-up2/comt-down2 to obtain the comt fragment derived from *Arabidopsis thaliana* with a seamless coloning homologous arm and RBS ligated with tktA.

With a codon-optimized car gene fragment (as shown by SEQ ID NO. 86) of *Mycobacterium marinum* synthesized by Beijing Genomics Institute as a template, the fragment car is amplified with primers car-up2/car-down2 to obtain the car fragment derived from *Mycobacterium marinum* with a seamless coloning homologous arm and RBS ligated with met2.

With a codon-optimized sfp fragment (as shown by SEQ ID NO. 87) of *Nocardia* iowensis synthesized by Beijing Genomics Institute as a template, the fragment sfp is amplified with primers sfp-up2/sfp-down2 to obtain the sfp fragment drived from *Nocardia* iowensis with a seamless coloning homologous arm and RBS ligated with car and plasmid.

With the genome DNA of *Escherichia coli* k12 as a template, a fragment metE (Gene ID: 948323) is amplified with primers met E-up2/metE-down2 to obtain the metE fragment derived from *Escherichia coli* with a seamless coloning homologous arm and RBS ligated with ahcY and plasmid.

With the genome DNA of *Escherichia coli* k12 as a template, a fragment metK (Gene ID: 945389) is amplified with primers metK-up2/metK-down2 to obtain the metK fragment derived from *Escherichia coli* with a seamless coloning homologous arm and RBS ligated with plasmid.

With the genome DNA of *Saccharomyces cerevisiae* S288C as a template, a fragment met2 (Gene ID: 855444) is amplified with primers met2-up2/met2-down2 to obtain the met2 fragment derived from *Saccharomyces cerevisiae* S288C with a seamless coloning homologous arm and RBS ligated with metK.

With the genome DNA of *Corynebacterium glutamicum* ATCC13032 as a template, the fragment ahcY (as shown by SEQ ID NO. 52) is amplified with primers ahcY-up2/ahcY-down2 to obtain an ahcY fragment derived from *Corynebacterium glutamicum* with a seamless coloning homologous arm and RBS ligated with comt.

The primer sequences are as follows:

```
tktA-up2:
                                        SEQ ID NO. 88
5'-ACGCCGAGCAGCAGCCAAGTAAAAGGAGGATATACATGTGG
ACACCAAGGCTGTAGA-3';;

tktA-down2:
                                        SEQ ID NO. 89
5'-TTAACCGTTAATGGAGTCCTTGG-3';;

aroG-up2:
                                        SEQ ID NO. 90
5'-GGAAACAGACCATGGAATTCAAGGAGGATATACATATGAGT
TCTCCAGTCTCACTCG-3';;

aroG-down2:
                                        SEQ ID NO. 91
5'-TTACTTGGCTGCTGCTCG-3';;

comt-up2:
                                        SEQ ID NO. 92
5'-CCAAGGACTCCATTAACGGTTAAAAGGAGGATATACATATG
GGTAGCACCGCGG-3';;

comt-down2:
                                        SEQ ID NO. 93
5'-TTACAGTTTTTTCAGCAGTTCAATCAGG-3';;

car-up2:
                                        SEQ ID NO. 94
5'-AAGAAGTTACCAACTGGTAGtctagaAAGGAGGATATACATATGT
CCCCAATCACCCGC-3';;

Car-down2:
                                        SEQ ID NO. 95
5'-TTGGATCCTTACAGCAGGCCCAGCAGG-3';;

sfp-up2:
                                        SEQ ID NO. 96
5'-CTGCTGGGCCTGCTGTAAggatccAAGGAGGATATACATATGATC
GAAACCATCCTG-3';;

sfp-down2:
                                        SEQ ID NO. 97
5'-CGCCAAAACAGCCAAGCTGAATTCGAGCTCGGTACCCTTAT
GCGTATGCGATTGCGGTC-3';;

metE-up2:
                                        SEQ ID NO. 98
5'-CGGAGCACTACCGCTACTAAAAGGAGGATATACATATGACA
ATATTGAATCACACCCTCG-3';;

metE-down2:
                                        SEQ ID NO. 99
5'-GACTCTAGAGGATCCCCGGGTACCGAGCTCTTACCCCCG
ACGCAAGTTC-3';;
```

-continued

```
metK-up2:
                                        SEQ ID NO. 100
5'-TTAATTAAGCTTGCATGCCTGCAGGTCGACAAGGAGGATAT
ACATATGGCAAAACACCTTTTTACGTC-3';;

metK-down2:
                                        SEQ ID NO. 101
5'-TTACTTCAGACCGGCAGCA-3';;

met2-up2:
                                        SEQ ID NO. 102
5'-GCTGCCGGTCTGAAGTAAAAGGAGGATATACATATGTCGCA
TACTTTAAAATCGAAAACG-3';;

met2-down2:
                                        SEQ ID NO. 103
5'-CTACCAGTTGGTAACTTCTTCGG-3';;

ahcY-up2:
                                        SEQ ID NO. 104
5'-ATTGAACTGCTGAAAAAACTGTAAAAGGAGGATATACATAT
GGACTTCAAGGTTGCCGA-3';;

ahcY-down2:
same as ahcY-down.
```

The gene amplification system and the gene amplification procedure are the same as above.

PCR products are subjected to agarose gel electrophoresis and product recovery to obtain corresponding gene products from different sources, such as tkt, aroG, comt, car, sfp, metE, metK, metX and ahcY.

The plasmid vector pEC-XK99E is linearized with the primers pec-F and pec-R to obtain a pec vector, the same as embodiment 1.

The ligation system, procedure, transformation and verification are the same as Embodiment 1. A correct single colony is selected, and named *Escherichia coli* WJ102; and after propagation and plasmid extraction, WJ102 plasmid is obtained.

The plasmid vector pXMJ19 is linearized with the primers px-F and px-R to obtain a pxmj vector, the same as embodiment 1.

The ligation system, procedure, transformation and verification are the same as embodiment 1. A correct single colony is selected, and named *Escherichia coli* WJ202; and after propagation and plasmid extraction, WJ202 plasmid is obtained.

Figure 3:
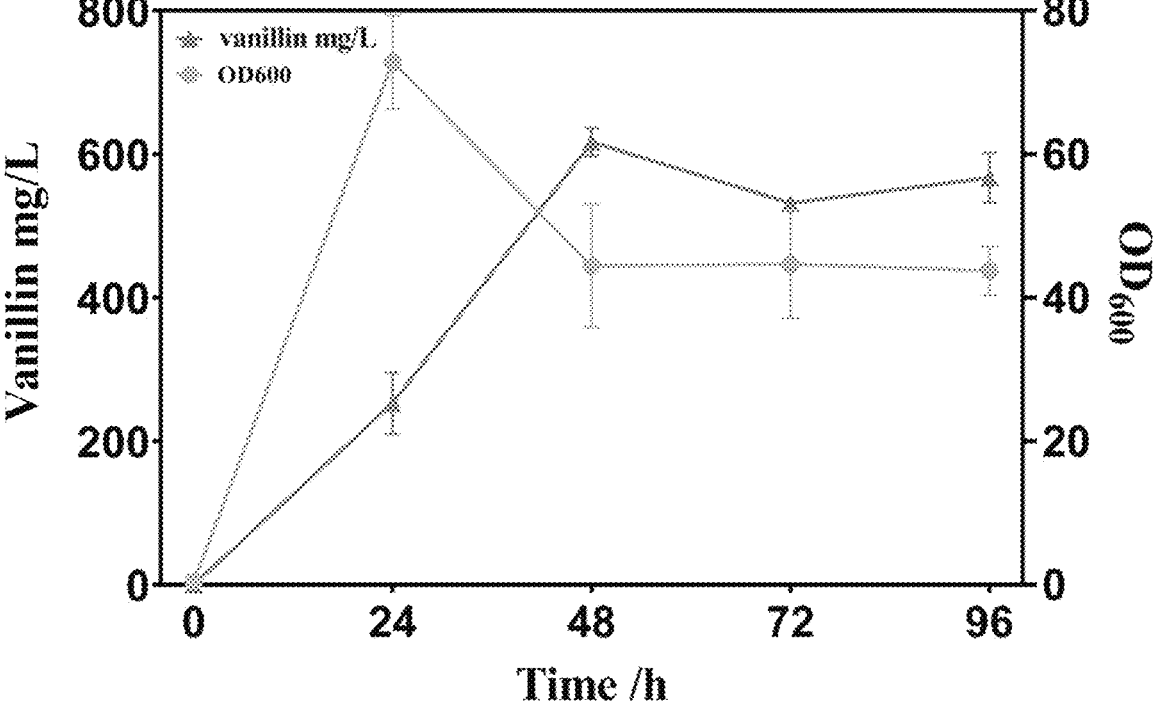
FIG. 3 shows a yield and biomass $OD_{600}$ of vanillin synthesized by genetically engineered bacteria constructed in embodiment 2 of the present invention by shaking flask fermentation with glucose as substrate at different times.

The *Escherichia coli* WJ102 plasmid and the *Escherichia coli* WJ202 plasmid are electrotransformed into competence of *Corynebacterium glutamicum* CG004 at the same time (prepared in a same way as embodiment 1), and named *Corynebacterium glutamicum* CG102. The competence preparation, electrotransformation, verification and fermentation are the same as embodiment 1. Results are shown in Table 2 and FIG. 3.

TABLE 2

| Time (h) | Vanillin (mg/L) | OD$_{600}$ |
|---|---|---|
| 0 | 0 | 0.468 |
| 24 | 252.87 | 72.8 |
| 48 | 616.60 | 44.4 |
| 72 | 531.45 | 44.7 |
| 96 | 566.96 | 43.7 |

Embodiment 3

A method for constructing a genetically engineered bacterium using glucose as a substrate for de novo synthesis of vanillin includes the following steps:

With the genome DNA of *Saccharomyces cerevisiae* S288C as a template, a fragment tk11 (Gene ID: 856188) is amplified with primers tk11up3/tk11-down3 to obtain atk11 fragment derived from *Saccharomyces cerevisiae* S288C with a seamless coloning homologous arm and RBS ligated with aro4.

With the genome DNA of *Saccharomyces cerevisiae* S288C as a template, a fragment aro4 (Gene ID: 852551) is amplified with primers aro4-up3/aro4-down3 to obtain a aro4 fragment derived from *Saccharomyces cerevisiae* S288C with a seamless coloning homologous arm and RBS ligated with plasmid.

With a codon-optimized comt fragment (as shown by SEQ ID NO. 105) of *Homo sapiens* synthesized by Beijing Genomics Institute as a template, the fragment comt is amplified with primers comt-up3/comt-down3 to obtain a comt fragment derived from *Homo sapiens* with a seamless coloning homologous arm and RBS ligated with tk11.

With a codon-optimized car gene fragment (as shown by SEQ ID NO. 47) of *Nocardia* iowensis synthesized by Beijing Genomics Institute as a template, the fragment car is amplified with primers car-up3/car-down3 to obtain a car fragment derived from *Nocardia* iowensis with a seamless coloning homologous arm and RBS ligated with met2.

With a codon-optimized sfp gene fragment (as shown by SEQ ID NO. 106) of *Bacillus subtilis* synthesized by Beijing Genomics Institute as a template, the fragment sfp is amplified with primers sfp-up3/sfp-down3 to obtain a sfp fragment derived from *Bacillus subtilis* with a seamless coloning homologous arm and RBS ligated with car and plasmid.

With the genome DNA of *Saccharomyces cerevisiae* S288C as a template, a fragment met6 (Gene ID: 856825) is amplified with primers met6-up3/met6-down3 to obtain a met6 fragment derived from *Saccharomyces cerevisiae* S288C with a seamless coloning homologous arm and RBS ligated with ahcY and plasmid.

With the genome DNA of *Saccharomyces cerevisiae* S288C as a template, the fragment SAM2 (Gene ID: 852113) is amplified with primers SAM2-up3/SAM2-down3 to obtain a SAM2 fragment derived from *Saccharomyces cerevisiae* S288C with a seamless coloning homologous arm and RBS ligated with plasmid.

With the genome DNA of *Saccharomyces cerevisiae* S288C as a template, the fragment met2 (Gene ID: 855444) is amplified with primers met2-up3/met2-down3 to obtain a met2 fragment derived from *Saccharomyces cerevisiae* S288C with a seamless coloning homologous arm and RBS ligated with SAM2.

With the genome DNA of *Corynebacterium glutamicum* ATCC13032 as a template, the fragment ahcY (as shown by SEQ ID NO. 52) is amplified with primers ahcY-up3/ahcY-down3 to obtain an ahcY fragment derived from *Corynebacterium glutamicum* with a seamless coloning homologous arm and RBS ligated with comt.

The primer sequences are as follows:

```
tk11up3:
                             SEQ ID NO. 107
5'-AGAGAAGTTAACAAGAAATAGAAGGAGGATATACATATGACT
CAATTCACTGACATTGATAAGC-3';;

tk11-down3:
                             SEQ ID NO. 108
5'-TTAGAAAGCTTTTTTCAAAGGAGAAATTAGC-3';;
```

-continued

```
aro4-up3:
                             SEQ ID NO. 109
5'-GGAAACAGACCATGGAATTCAAGGAGGATATACATATGAGT
GAATCTCCAATGTTCGC-3';;

aro4-down3:
                             SEQ ID NO. 110
5'-CTATTTCTTGTTAACTTCTCTTCTTTGTCTG-3';;

comt-up3:
                             SEQ ID NO. 111
5'-CTCCTTTGAAAAAAGCTTTCTAAAAGGAGGATATACATATG
CCGGAAGCCCCG-3';;

comt-down3:
                             SEQ ID NO. 112
5'-TTACGGACCCGCTTCACTACC-3';;

car-up3:
                             SEQ ID NO. 113
5'-AAGAAGTTACCAACTGGTAGTCTAGAAAGGAGGATATACATA
TGGCAGTGGATTCCCCAG-3';;

car-down3:
same as car-down;

sfp-up3:
                             SEQ ID NO. 114
5'-CTGCTGCAGCTGCTGTAAGGATCCCCAAGGAGGATATACATA
TGAAGATCTACGGCATC-3';;

sfp-down3:
                             SEQ ID NO. 115
5'-CTGAATTCGAGCTCGGTACCCTTACAGCAGTTCTTCGTAGG
ACAC-3';;

met6-up3:
                             SEQ ID NO. 116
5'-CGGAGCACTACCGCTACTAAAAGGAGGATATACATATGGTT
CAATCTGCTGTCTTAGG-3';;

met6-down3:
                             SEQ ID NO. 117
5'-TCTAGAGGATCCCCGGGTACCGAGCTCTTAATTCTTGTAT
TGTTCACGGAAGTACTTG-3';;

SAM2-up3:
                             SEQ ID NO. 118
5'-TTAAGCTTGCATGCCTGCAGGTCGACAAGGAGGATATACA
TATGTCCAAGAGCAAAACTTTCTTAT-3';;

SAM2-down3:
                             SEQ ID NO. 119
5'-TTAAAATTCCAATTTCTTTGGTTTTTCCC-3';;

met2-up3:
                             SEQ ID NO. 120
5'-CCAAAGAAATTGGAATTTTAAAAGGAGGATATACATATGTC
GCATACTTTAAAATCGAAAACG-3';;

met2-down3:
same as met2-down2;

ahcY-up3:
                             SEQ ID NO. 121
5'-GGTAGTGAAGCGGGTCCGTAAAAGGAGGATATACATATGG
ACTTCAAGGTTGCCGA-3';;

ahcY-down3:
same as ahcY-down.
```

The gene amplification system and the gene amplification procedure are the same as above.

PCR products are subjected to agarose gel electrophoresis and product recovery to obtain corresponding gene products from different sources, such as tk11, aro4, comt, car, sfp, met6, SAM2, met2 and ahcY.

The plasmid vector pEC-XK99E is linearized with the primers pec-F and pec-R to obtain a pec vector, the same as embodiment 1.

The ligation system, procedure, transformation and verification are the same as embodiment 1. A correct single colony is selected, and named *Escherichia coli* WJ103; and after propagation and plasmid extraction, WJ103 plasmid is obtained.

The plasmid vector pXMJ19 is linearized with the primers px-F and px-R to obtain a pxmj vector, the same as embodiment 1.

The ligation system, procedure, transformation and verification are the same as embodiment 1. A correct single colony is selected, and named *Escherichia coli* WJ203; and after propagation and plasmid extraction, WJ203 plasmid is obtained.

Figure 4:
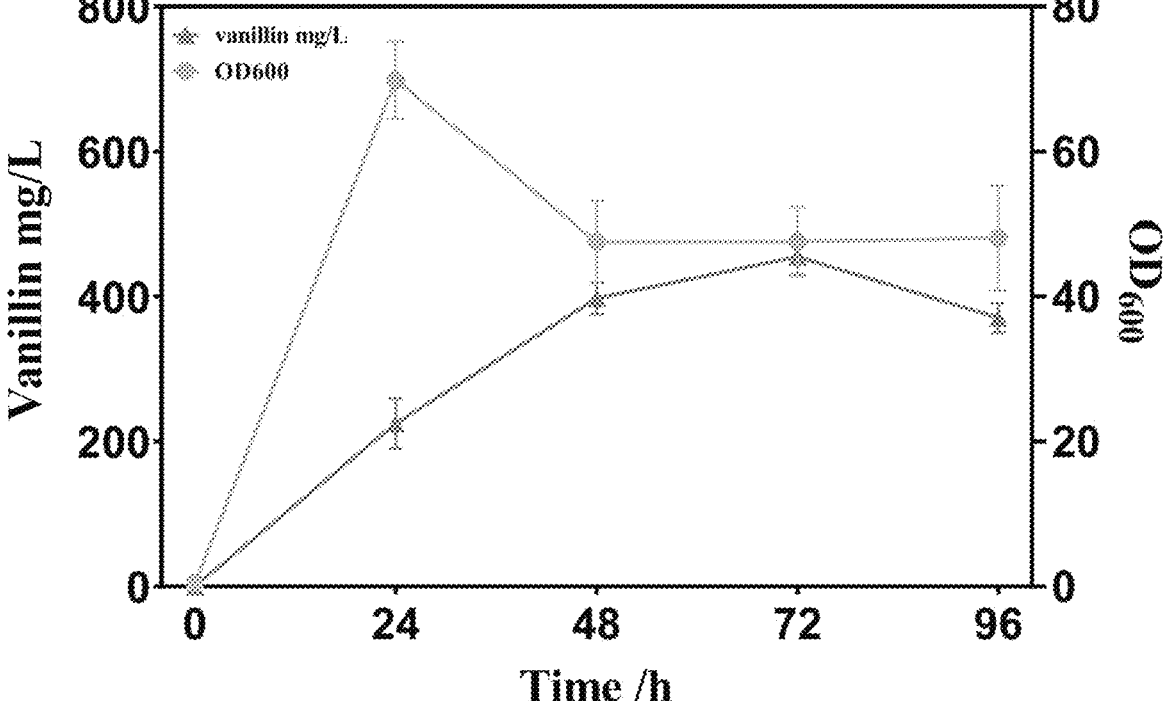
FIG. 4 shows a yield and biomass $OD_{600}$ of vanillin synthesized by genetically engineered bacteria constructed in embodiment 3 of the present invention by shaking flask fermentation with glucose as substrate at different times.

The *Escherichia coli* WJ103 plasmid and the *Escherichia coli* WJ203 plasmid are electrotransformed into competence of *Corynebacterium glutamicum* CG004 at the same time (prepared in a same way as Embodiment 1), and named *Corynebacterium glutamicum* CG103. The competence preparation, electrotransformation, verification and fermentation are the same as Embodiment 1. Results are shown in Table 3 and FIG. 4.

TABLE 3

| Time (h) | Vanillin (mg/L) | OD$_{600}$ |
|---|---|---|
| 0 | 0 | 0.466 |
| 24 | 224.83 | 69.9 |
| 48 | 397.38 | 47.5 |
| 72 | 454.82 | 47.6 |
| 96 | 370.38 | 48.1 |

Embodiment 4

A method for constructing a genetically engineered bacterium using glucose as a substrate for de novo synthesis of vanillin includes the following steps:

With the genome DNA of *Bacillus subtilis* 168 as a template, a fragment tktA (Gene ID: 937377) is amplified with primers tktA-up4/tktA-down4 to obtain a tktA fragment derived from *Bacillus subtilis* 168 with a seamless coloning homologous arm and ribosome bind site (RBS) ligated with aroX.

With the genome DNA of *Bacillus subtilis*168 as a template, a fragment aroX (Gene ID: 937853) is amplified with primers aroX-up4/aroX-down4 to obtain an aroX fragment derived from *Bacillus subtilis* 168 with a seamless coloning homologous arm and RBS ligated with plasmid.

With a codon-optimized comt fragment (as shown by SEQ ID NO. 122) of *Coffea canephora* (*Robusta* coffee) synthesized by Beijing Genomics Institute as a template, the fragment comt is amplified with primers comt-up4/comt-down4 to obtain a comt fragment derived from *Coffea canephora* with a seamless coloning homologous arm and RBS ligated with tktA.

With a codon-optimized car gene fragment (as shown by SEQ ID NO. 47) of *Nocardia* iowensis synthesized by Beijing Genomics Institute as a template, the fragment car is amplified with primers car-up4/car-down4 to obtain a car fragment derived from *Nocardia* iowensis with a seamless coloning homologous arm and RBS ligated with metAA.

With a codon-optimized sfp fragment (as shown in SEQ ID NO. 48) of *Mycobacterium marinum* synthesized by Beijing Genomics Institute as a template, the fragment sfp is amplified with primers sfp-up4/sfp-down4 to obtain a sfp fragment derived from *Mycobacterium marinum* with a seamless coloning homologous arm and RBS ligated with car and plasmid.

With the genome DNA of *Bacillus subtilis* 168 as a template, the fragment metE (Gene ID: 936480) is amplified with primers metE-up4/metE-down4 to obtain a metE fragment derived from *Bacillus subtilis* 168 with a seamless coloning homologous arm and RBS ligated with ahcY and plasmid.

With the genome DNA of *Bacillus subtilis*168 as a template, the fragment metK (Gene ID: 937090) is amplified with primers metK-up4/metK-down4 to obtain a metK fragment derived from *Bacillus subtilis* 168 with a seamless coloning homologous arm and RBS ligated with plasmid.

With the genome DNA of *Bacillus subtilis*168 as a template, the fragment metAA (Gene ID: 939083) is amplified with primers metAA-up4/metAA-down4 to obtain a metAA fragment derived from *Bacillus subtilis* 168 with a seamless coloning homologous arm and RBS ligated with metK.

With the genome DNA of *Corynebacterium glutamicum* ATCC13032 as a template, the fragment ahcY (as shown by SEQ ID NO. 52) is amplified with primers ahcY-up4/ahcY-down4 to obtain a ahcY fragment derived from *Corynebacterium glutamicum* with a seamless coloning homologous arm and RBS ligated with comt.

The primer sequences are as follows:

```
tktA-up4:
                                    SEQ ID NO. 123
5'-CAATGGTGAAAGTCAACGCTTAAAAGGAGGATATACATATG
GATACAATTGAAAAGAAATCAGTTGC-3';;

tktA-down4:
                                    SEQ ID NO. 124
5'-TTACTTATTGATTAATGCCTTAACTCGATTC-3';;

aroX-up4:
                                    SEQ ID NO. 125
5'-GGAAACAGACCATGGAATTCAAGGAGGATATACATATGAGC
AACACAGAGTTAGAGC-3';;

aroX-down4:
                                    SEQ ID NO. 126
5'-TTAAGCGTTGACTTTCACCATTG-3';;

comt-up4:
                                    SEQ ID NO. 127
5'-AGGCATTAATCAATAAGTAAAAGGAGGATATACATATGGCC
GAAGAAGAAGCATG-3';;

comt-down4:
                                    SEQ ID NO. 128
5'-TTATTTACACAGTTCCATAATCCAGGTATTC-3';;

car-up4:
                                    SEQ ID NO. 129
5'-TCCTTATGAATGGGACTAAtctagaAAGGAGGATATACATATGGCAGT
GGATTCCCCAG-3';;

car-down4:
same as car-down1;

sfp-up4:
same as sfp-up 1;

sfp-down4:
same as sfp-down 1;

metE-up4:
                                    SEQ ID NO. 130
5'-CGGAGCACTACCGCTACTAAAAGGAGGATATACATATGACA
ACCATCAAAACATCGAAT-3';;
```

-continued

```
metE-down4:
                                   SEQ ID NO. 131
5'-TCTAGAGGATCCCCGGGTACCGAGCTCTTATACTAGCTGTGTCTGCTG
TGC-3';;

metK-up4:
                                   SEQ ID NO. 132
5'-TTAAGCTTGCATGCCTGCAGGTCGACAAGGAGGATATACAT
ATGAGTAAAAATCGTCGTTTATTTACATC-3';;

metK-down4:
                                   SEQ ID NO. 133
5'-TTATTCTCCTAACGCTTCTTTACGC-3';;

metAA-up4:
                                   SEQ ID NO. 134
5'-AAGAAGCGTTAGGAGAATAAAAGGAGGATATACATTTGC
CTATTAATATACCAACACACCTG-3';;

metAA-down4:
                                   SEQ ID NO. 135
5'-TTAGTCCCATTCATAAGGAGTTTCTTG-3';;

ahcY-up4:
                                   SEQ ID NO. 136
5'-TTATGGAACTGTGTAAATAAAAGGAGGATATACATATGGACTTCAAGG
TTGCCGA-3';;

ahcY-down4:
same as ahcY-down.
```

The gene amplification system and the gene amplification procedure are the same as above.

PCR products are subjected to agarose gel electrophoresis and product recovery to obtain corresponding gene products from different sources, such as tktA, aroX, comt, car, sfp, metE, metK, metAA and ahcY.

The plasmid vector pEC-XK99E is linearized with the primers pec-F and pec-R to obtain a pec vector, the same as embodiment 1.

The ligation system, procedure, transformation and verification are the same as embodiment 1. A correct single colony is selected, and named *Escherichia coli* WJ104; and after propagation and plasmid extraction, WJ104 plasmid is obtained.

The plasmid vector pXMJ19 is linearized with the primers px-F and px-R to obtain a pxmj vector, the same as embodiment 1.

The ligation system, procedure, transformation and verification are the same as embodiment 1. A correct single colony is selected, and named *Escherichia coli* WJ204; and after propagation and plasmid extraction, WJ204 plasmid is obtained.

Figure 5:
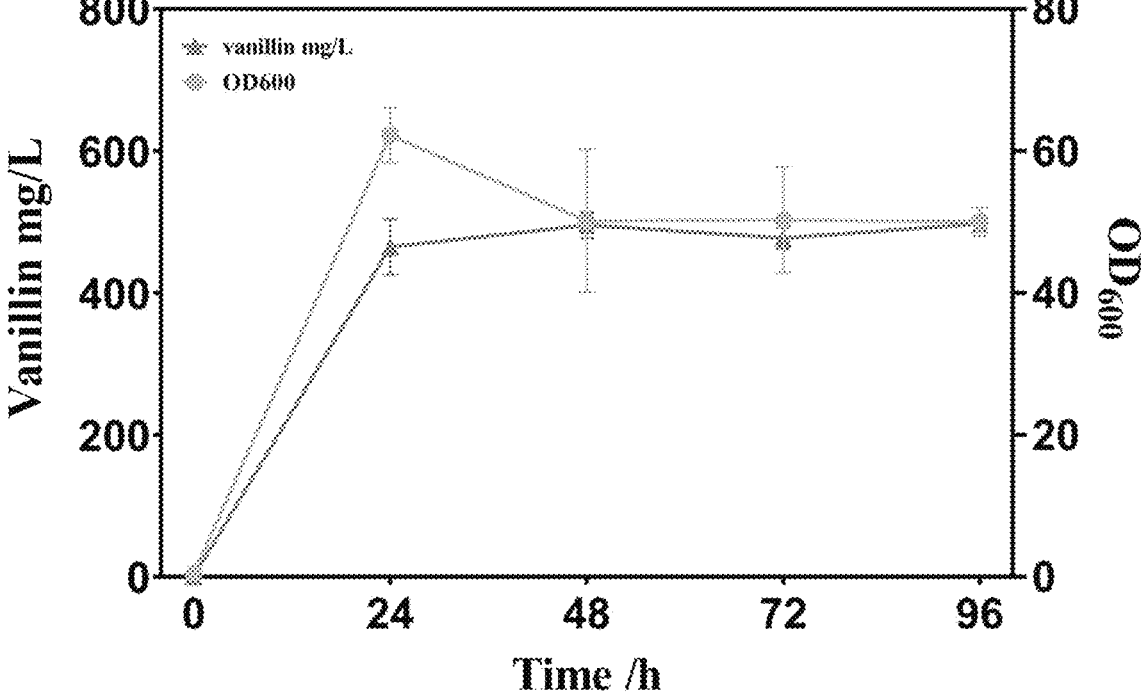
FIG. 5 shows a yield and biomass $OD_{600}$ of vanillin synthesized by genetically engineered bacteria constructed in embodiment 4 of the present invention by shaking flask fermentation with glucose as substrate at different times.

The *Escherichia coli* WJ104 plasmid and the *Escherichia coli* WJ204 plasmid are electrotransformed into competence of *Corynebacterium glutamicum* CG104 at the same time (prepared in a same way as embodiment 1), and named *Corynebacterium glutamicum* CG104. The competence preparation, electrotransformation, verification and fermentation are the same as embodiment 1. Results are shown in Table 4 and FIG. 5.

TABLE 4

| Time (h) | Vanillin (mg/L) | OD$_{600}$ |
|---|---|---|
| 0 | 0 | 0.464 |
| 24 | 464.72 | 61.7 |
| 48 | 495.19 | 52.1 |
| 72 | 477.08 | 50.6 |
| 96 | 497.08 | 49.9 |

Embodiment 5

A method for constructing a genetically engineered bacterium using glucose as a substrate for de novo synthesis of vanillin includes the following steps:

With a codon-optimized comt fragment (as shown by SEQ ID NO. 137) of *Mus musculus* synthesized by Beijing Genomics Institute is as a template, the fragment comt is amplified with primers comt-up5/comt-down4 to obtain a comt fragment derived from *Mus musculus* with a seamless coloning homologous arm and RBS ligated with tktA.

The primer sequences are as follows:

```
comt-up5:
                                   SEQ ID NO. 138
5'-AAAGCAAAAGAACTGCTGTAAAAGGAGGATATACATATGCT
GCTGGCGGCC-3';;

comt-down4:
                                   SEQ ID NO. 139
5'-TTAGCTTTTAACCGGGCTGCT-3';;

ahcY-up5:
                                   SEQ ID NO. 140
5'-AGCAGCCCGGTTAAAAGCTAAAAGGAGGATATACATATGG
ACTTCAAGGTTGCCGA-3';.
```

Other genes and primers are the same as embodiment 1.

The gene amplification system and the gene amplification procedure are the same as above.

PCR products are subjected to agarose gel electrophoresis and product recovery to obtain corresponding gene products from different sources, such as tktA, aroG, comt, car, sfp, metE, metK, metX and ahcY.

The plasmid vector pEC-XK99E is linearized with the primers pec-F and pec-R to obtain a pec vector, the same as embodiment 1.

The ligation system, procedure, transformation and verification are the same as embodiment 1. A correct single colony is selected, and named *Escherichia coli* WJ105; and after propagation and plasmid extraction, WJ105 plasmid is obtained.

Figure 6:
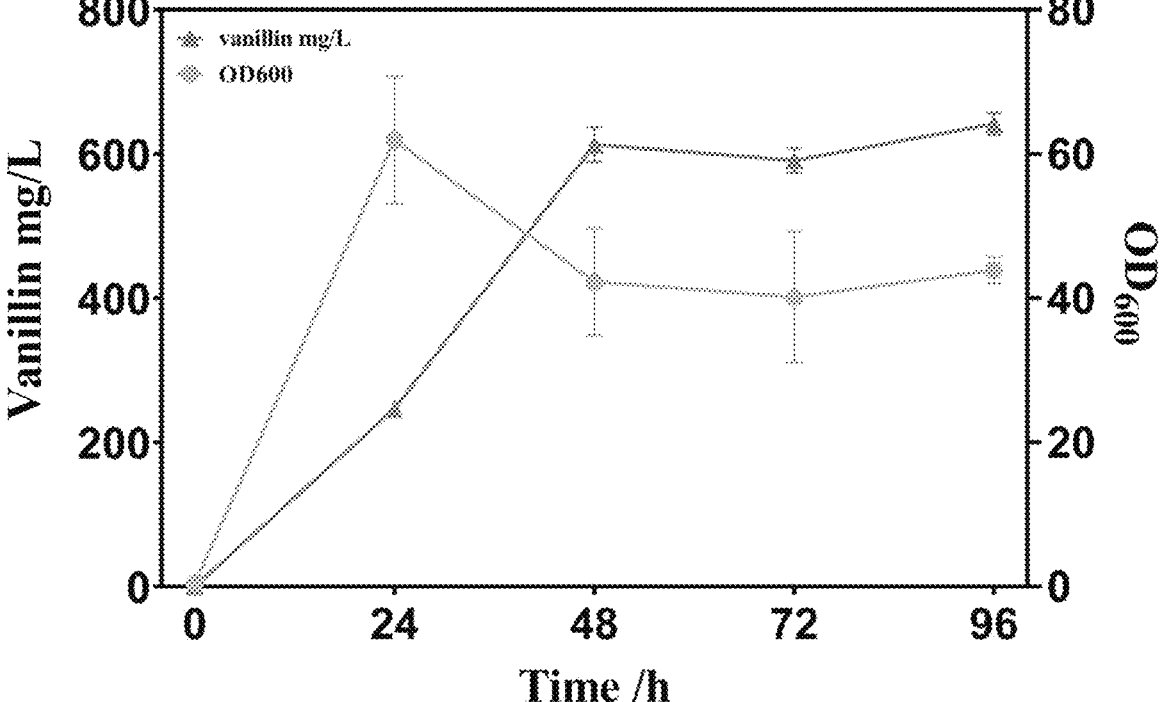
FIG. 6 shows a yield and biomass $OD_{600}$ of vanillin synthesized by genetically engineered bacteria constructed in embodiment 5 of the present invention by shaking flask fermentation with glucose as substrate at different times.

The *Escherichia coli* WJ105 plasmid and the *Escherichia coli* WJ201 plasmid are electrotransformed into competence of *Corynebacterium glutamicum* CG004 at the same time (prepared in a same way as embodiment 1), and named *Corynebacterium glutamicum* CG105. The competence preparation, electrotransformation, verification and fermentation are the same as embodiment 1. Results are shown in Table 5 and FIG. 6.

TABLE 5

| Time (h) | Vanillin (mg/L) | OD$_{600}$ |
|---|---|---|
| 0 | 0 | 0.470 |
| 24 | 246.97 | 60.53 |
| 48 | 601.81 | 43.19 |
| 72 | 590.10 | 42.18 |
| 96 | 633.39 | 44.27 |

The peak time of HPLC detection results of vanillin specimen is 17.231 min, the peak time of fermentation culture products of genetically engineered strains prepared in Embodiments 1-5 is 17.233 min, and the peak time of fermentation samples of engineered strains is the same as that of the vanillin specimen, which proves that the fermentation products of engineered strains are the target product-vanillin.

The above description of the disclosed embodiments enables those skilled in the art to implement or use the present invention. Various modifications to these embodiments are apparent for those skilled in the art. The general principles defined herein may be implemented in other embodiments without departing from the spirit or scope of the present invention. Therefore, the present invention will not be limited to these embodiments described herein, but shall conform to the widest scope consistent with the principles and novel characteristics disclosed herein.

---

What is claimed is:

1. A genetically engineered bacterium that uses glucose as a substrate for de novo synthesis of vanillin, wherein the genetically engineered bacterium is a recombinant *Corynebacterium glutamicum* comprising a vanillin synthesis module and a methyl cyclic regeneration module;

wherein the recombinant *Corynebacterium glutamicum* is a variant of a *Corynebacterium glutamicum* ATCC13032 cell obtained by knocking out the pcaHG, van, vdh and fud genes in said *Corynebacterium glutamicum* ATCC13032 cell, wherein the fud gene is an alcohol dehydrogenase (NADP+) gene, the alcohol dehydrogenase (NADP+) gene being a Zn-dependent alcohol dehydrogenase gene;

wherein the vanillin synthesis module comprises a transketolase gene, a 3-deoxy-7-phosphoheptulonate synthase gene, an O-methyltransferase gene, a carboxylic acid reductase gene and a 4'-phosphopantetheinyl transferase gene;

wherein the methyl cyclic regeneration module comprises a 5-methyltetrahydropteroyltriglutamate-homocysteine methyltransferase gene, an S-adenosylmethionine synthase gene, a homoserine O-acetyltransferase gene and an adenosylhomocysteinase gene;

wherein the recombinant *Corynebacterium glutamicum* expresses any one of the combinations of genes selected from:

(a) an *Escherichia coli* tktA gene, an *Escherichia coli* K12 3-deoxy-7-phosphoheptulonate synthase gene having the sequence of SEQ ID NO: 45, a *Rattus norvegicus* O-methyltransferase gene having the sequence of SEQ ID NO: 46, a *Nocardia* iowensis carboxylic acid reductase gene having the sequence of SEQ ID NO: 47, a *Mycobacterium marinum* 4'-phosphopantetheinyl transferase gene having the sequence of SEQ ID NO: 48, an endogenous *Corynebacterium glutamicum* 5-methyltetrahydropteroyltriglutamate-homocysteine methyltransferase gene having the sequence of SEQ ID NO: 49, an endogenous *Corynebacterium glutamicum* S-adenosylmethionine synthase gene having the sequence of SEQ ID NO: 50, an endogenous *Corynebacterium glutamicum* homoserine O-acetyltransferase gene having sequence of SEQ ID NO: 51, and an endogenous *Corynebacterium glutamicum* adenosylhomocysteinase gene having the sequence of SEQ ID NO: 52;

(b) an endogenous *Corynebacterium glutamicum* transketolase gene having the sequence of SEQ ID NO: 83, an endogenous *Corynebacterium glutamicum* 3-deoxy-7-phosphoheptulonate synthase gene having the sequence of SEQ ID NO: 84, an *Arabidopsis thaliana* O-methyltransferase gene having the sequence of SEQ ID NO: 85, a *Mycobacterium marinum* carboxylic acid reductase gene having the sequence of SEQ ID NO: 86, a *Nocardia* iowensis 4'-phosphopantetheinyl transferase gene having the sequence of SEQ ID NO: 87, an *Escherichia coli* K12 metE gene, an *Escherichia coli* K12 metK gene, a *Saccharomyces cerevisiae* S288C met2 gene, and an endogenous *Corynebacterium glutamicum* adenosylhomocysteinase gene having the sequence of SEQ ID NO: 52;

(c) a *Saccharomyces cerevisiae* S288C tkl1 gene, a *Saccharomyces cerevisiae* S288C aro4 gene, s *Homo sapiens* O-methyltransferase gene having the sequence of SEQ ID NO: 105, a *Nocardia* iowensis carboxylic acid reductase gene having the sequence of SEQ ID NO: 47, a *Bacillus subtilis* 4'-phosphopantetheinyl transferase gene having the sequence of SEQ ID NO: 106, a *Saccharomyces cerevisiae* S288C met6 gene, a *Saccharomyces cerevisiae* S288C SAM2 gene, a *Saccharomyces cerevisiae* S288C met2 gene, and an endogenous *Corynebacterium glutamicum* adenosylhomocysteinase gene having the sequence of SEQ ID NO: 52; and (d) an *Escherichia coli* tktA gene, an *Escherichia coli* K12 3-deoxy-7-phosphoheptulonate synthase gene having the sequence of SEQ ID NO: 45, a *Mus musculus* O-methyltransferase gene having the sequence of SEQ ID NO: 137, a *Nocardia* iowensis carboxylic acid reductase gene having the sequence of SEQ ID NO: 47, a *Mycobacterium marinum* 4'-phosphopantetheinyl transferase gene having the sequence of SEQ ID NO: 48, an endogenous *Corynebacterium glutamicum* 5-methyltetrahydropteroyltriglutamate-homocysteine methyltransferase gene having the sequence of SEQ ID NO: 49, an endogenous *Corynebacterium glutamicum* S-adenosylmethionine synthase gene having the sequence of SEQ ID NO: 50, an endogenous *Corynebacterium glutamicum* homoserine O-acetyltransferase gene having sequence of SEQ ID NO: 51, and an endogenous *Corynebacterium glutamicum* adenosylhomocysteinase gene having the sequence of SEQ ID NO: 52.

2. A method for constructing the genetically engineered bacterium that uses glucose as a substrate for de novo synthesis of vanillin according to claim 1, wherein said method comprises:

(i) disrupting the endogenous pcaHG, van, vdh, and fud genes in a *Corynebacterium glutamicum* ATCC13032 cell, wherein the fud gene is an alcohol dehydrogenase (NADP$^+$) gene, the alcohol dehydrogenase (NADP$^+$) gene being a Zn-dependent alcohol dehydrogenase gene, and (ii) transforming the *Corynebacterium glutamicum* of (i) with any one of the combinations of genes selected from (a), (b), (c) and (d).

* * * * *

SEQUENCE LISTING

```
Sequence total quantity: 140
SEQ ID NO: 1            moltype = DNA  length = 1000
FEATURE                 Location/Qualifiers
source                  1..1000
                        mol_type = other DNA
                        organism = synthetic construct
SEQUENCE: 1
ccatcgcatt gccgaaaagc tgacaccgcg cattgctggc caggcactga tggaagcctc   60
cgcacttgca gggctgatta ctcgctggat caaggaactg gatccaacct tcacaggaaa  120
gaagcgtggg ccaaagggga gtgatggcac cttgactttc cgccacgtgg acgggcgtac  180
gtacatcagt ggaaatattg acggtgtcac cggcaagctg ttccaaaaag ctctggaaaa  240
agtgaaacag aagggcgagg acctcgcgcg ggccctggtc accttcctgg cggggcggac  300
caaagtgaaa atcgtcagcg cggtatacac gccctggtg ggtggcgtgt cctggattcc  360
gggggtggga ttcctgagtc aagaggagtc ccggaagctg ggtaagactg cctcgaaggt  420
cattgacctg gatacgatcg ccactcgtgt ggaaaatggc tacaccccaa gtcccgagct  480
acgcctttat gtgatggggc gggacggcac ctgtaggcat ccgggctgca cggtgtctgc  540
cgacaactgc cagatcgatc acgtgatccc gttcggtgag ggtgggttga ctgtggcctg  600
gaacttgcag tgcctctgcg cgcatcatca caatatgaag actgatgggc gcatccaggc  660
ggcgattgat tccatgggtc gggtcgcctg gattgggccg tgcaatcgca cagtggtaac  720
cgaacctgtc ggaccgttgg cgcaagagat gcccacgggg cagtggggc agactctgga  780
agcacggatg gagaagactt ttgaaaagct ccgcagttca ctcgaggtat tggatgacta  840
aaccctatg cacaccccta gttaacccct gaccttcggg gtttgcgctg gtggcgaatg  900
ttcgcgcgcg atctgacatg ttcgccccgc gaactacttg tcaacggcct caatcatccc  960
tactttgaga tctatatcac tagacgcaga aaggtctcgc                        1000

SEQ ID NO: 2            moltype = DNA  length = 1000
FEATURE                 Location/Qualifiers
source                  1..1000
                        mol_type = other DNA
                        organism = synthetic construct
SEQUENCE: 2
attgacccga tctttatact ccgaccttgc tggtagtgga gaacacctca gcagcctttc   60
cgacgagact ttcctaaaga atcttcttgt cgtggaggcc gctttggcgg ttgcagctgc  120
ccccgagcac gcagcaatgg cgaaggccac cattgattct tatcagttgg atgtggagga  180
gctttcccgt cgcgcagccg agggcggtaa tccgctcatt ccgctggtca ctgacctcaa  240
ggccatcaat ccggcaggca tccacattgg cgcaacgagc caggacatca ttgattctgc  300
gttaatgctg tgcatgaagg aaggggtggg ggaggtcgtc gacaagctta aaaagcttgc  360
gcgagatttg gccgagctca ccgcgggagca taaagcaacc ccgatcatgg ggcgcacgtt  420
ggggcagatc gcgacgccga cgacgttcgg cgcgctgacc ggcggctggc tggttgcggt  480
ggacaatgcg gcacgcgccc tggaggcgct ggagtttccg gtgtcgtatg gcggtgccag  540
cggaaatatg acggcggtgc acccgcgtgg cttcgagatt caggcgaagc tggccgagga  600
gttgggcctt tttgatccgc agtgggtgtg gcattccgat cgcacgccga tcactcgat   660
cgcgtcggcg ctggcaacgg ccgctggtgt ggtacgcaaa attgctggtg acgtggtgtt  720
ttactcacaa accgaggtcg gcgagttgcg ggagaaatcc cccggcggca gctccgcgat  780
gccccacaaa gccaatccgg ccgctgcgat tgcgtgcgac ggttacgcgc gccgggcacc  840
tggccttctt gcaacgcttt tcgacgccct cgactgccgt ttgcagcgcg cgcaccggcag  900
ctggcacgcg gagtgggcaa cgctgcgcga gttggctgct gtcactcact cagcagtgag  960
cagggctgca accagcatcg atggcatcac cgtcaacgtt                        1000

SEQ ID NO: 3            moltype = DNA  length = 29
FEATURE                 Location/Qualifiers
source                  1..29
                        mol_type = other DNA
                        organism = synthetic construct
SEQUENCE: 3
atgattacgc catcgcattg ccgaaaagc                                      29

SEQ ID NO: 4            moltype = DNA  length = 25
FEATURE                 Location/Qualifiers
source                  1..25
                        mol_type = other DNA
                        organism = synthetic construct
SEQUENCE: 4
ggtcaatgcg agacctttct gcgtc                                          25

SEQ ID NO: 5            moltype = DNA  length = 36
FEATURE                 Location/Qualifiers
source                  1..36
                        mol_type = other DNA
                        organism = synthetic construct
SEQUENCE: 5
```

-continued

```
aaaggtctcg cattgacccg atctttatac tccgac                                 36

SEQ ID NO: 6              moltype = DNA   length = 22
FEATURE                   Location/Qualifiers
source                    1..22
                          mol_type = other DNA
                          organism = synthetic construct
SEQUENCE: 6
ctcaacgttg acggtgatgc ca                                                22

SEQ ID NO: 7              moltype = DNA   length = 38
FEATURE                   Location/Qualifiers
source                    1..38
                          mol_type = other DNA
                          organism = synthetic construct
SEQUENCE: 7
atcaccgtca acgttgagct cggtagatcc tctagagt                              38

SEQ ID NO: 8              moltype = DNA   length = 36
FEATURE                   Location/Qualifiers
source                    1..36
                          mol_type = other DNA
                          organism = synthetic construct
SEQUENCE: 8
aatgcgatgg cgtaatcatg tcatagctgt ttcctg                                36

SEQ ID NO: 9              moltype = DNA   length = 23
FEATURE                   Location/Qualifiers
source                    1..23
                          mol_type = other DNA
                          organism = synthetic construct
SEQUENCE: 9
gcggataaca atttcacaca gga                                               23

SEQ ID NO: 10             moltype = DNA   length = 19
FEATURE                   Location/Qualifiers
source                    1..19
                          mol_type = other DNA
                          organism = synthetic construct
SEQUENCE: 10
cgggcctctt cgctattac                                                    19

SEQ ID NO: 11             moltype = DNA   length = 25
FEATURE                   Location/Qualifiers
source                    1..25
                          mol_type = other DNA
                          organism = synthetic construct
SEQUENCE: 11
cccatattac acgccatgat atgct                                             25

SEQ ID NO: 12             moltype = DNA   length = 29
FEATURE                   Location/Qualifiers
source                    1..29
                          mol_type = other DNA
                          organism = synthetic construct
SEQUENCE: 12
gcatgtaaat atcgttagac gtaatgccg                                        29

SEQ ID NO: 13             moltype = DNA   length = 19
FEATURE                   Location/Qualifiers
source                    1..19
                          mol_type = other DNA
                          organism = synthetic construct
SEQUENCE: 13
cgcgacttgc catcacatc                                                    19

SEQ ID NO: 14             moltype = DNA   length = 21
FEATURE                   Location/Qualifiers
source                    1..21
                          mol_type = other DNA
                          organism = synthetic construct
SEQUENCE: 14
gtcaagcagg ctaaaccgga g                                                 21

SEQ ID NO: 15             moltype = DNA   length = 939
FEATURE                   Location/Qualifiers
source                    1..939
                          mol_type = other DNA
                          organism = synthetic construct
```

-continued

```
SEQUENCE: 15
ataagctgct catgcttggc caggatgccg gcgccttccg tcctggaatc tccgcagaag    60
acgtactggt tcttattagc tttgaagaac ctctactccc ttgatttgga atcagaggcc   120
aatattgaag gcatgaagcg catcgtcgtt gacacggtgc tggcattctt gacctcaaat   180
attcaaaatt ctggcaactc cagctacctg gttgttggtg gcaagactgc agaaccagaa   240
actgatgaca gcgtctacag ctttgatacg gacgtgttcg aaaactaaag ggtatcgagt   300
agtttcaagc ccttttccgc ccattcaatc tctgcctgag cgcgtgcaat ctgcccctca   360
taggcaagca ctttaaacgc gactattcgc tcgtgctcct ttttcgggga gcgctcaagt   420
cgccgtgcca aggttggatg agtttttgct ttcagctcat caatcattga ttctgattga   480
attttctgct gttcaaaatg agcgatgtgc gcccttaaat gtcggcgtgc atcgccattt   540
gtaccgacct caaaataggc ggctttaagc ctggcaggat ctctggtggg accgtaggtt   600
actggctcgt accacgcttt tcttagcgct tcccagcctt tttcactcaa ggcgtattcg   660
gttttggtgg cgcctttgga gccccaggga acatcggatc ccacgaggag ttcttcggct   720
tccatttttc gaagttcggg ataaatctgc gaatcgaaac cactccacac aaagcccacc   780
gaggccccaa atcgctggga ggcgtcatac ccagtcaatg gtccggaact tagtagcaca   840
agtaatgcag atcgtagagt cacgtgctca ttgtcccata tctacccccg ctcccgagaa   900
tgaatacccg cagctcagag accccagctg acattaact                         939

SEQ ID NO: 16           moltype = DNA   length = 939
FEATURE                 Location/Qualifiers
source                  1..939
                        mol_type = other DNA
                        organism = synthetic construct
SEQUENCE: 16
cagcaatgtc gagatatcag tggttcattg tatttatcgc agtgctgctc aacgcactgg    60
acggctttga tgtcctcgcc atgtctttta ctgcgaatgc agtgaccgaa gaatttggac   120
tgagtggcag ccagcttggt gtgctgctga gttccgcgct gttcggcatg accgctggat   180
ctttgctgtt cggtccgatc ggtgaccgtt tcggccgtaa gaatgccctg atgatcgcgc   240
tgctgttcaa cgtggtggga ttggtattgt ccgccaccgc gcagtccgca ggccagttgg   300
gcgtgtggcg tttgatcact ggtatcggca tcggcggaat cctcgcctgc atcacagtgg   360
tgatcagtga gttctccaac aacaaaaacc gcggcatggc catgtccatc tacgctgctg   420
gttacggcat cggcgcgtcc ttgggcggtt tcggcgcagc gcagctcatc ccaacatttg   480
gatggcgctc cgtgttcgca gccggtgcga tcgcaactgg tatcgccacc atcgctactt   540
tcttcttcct gccagaatcc gttgattggc tgagcactcg ccgccctgcg ggcgctcgcg   600
acaagatcaa ttacattgcg cgccgcctgg gcaaagtcgg tacctttgag cttccaggcg   660
aacaaagctt gtcgacgaaa aaagccggtc tccaatcgta tgcagtgctc gttaacaaag   720
agaaccgtgg aaccagcatc aagctgtggg ttgcgttcgg catcgtgatg ttcggcttct   780
acttcgccaa cacttggacc ccgaagctgc tcgtggaaac cggaatgtca gaacagcagg   840
gcatcatcgg tggtttgatg ttgtccatgg gtggagcatt cggctccctg ctctacggtt   900
tcctcaccac caagttcagc tcccgaaaca cactgatga                         939

SEQ ID NO: 17           moltype = DNA   length = 41
FEATURE                 Location/Qualifiers
source                  1..41
                        mol_type = other DNA
                        organism = synthetic construct
SEQUENCE: 17
aacagctatg acatgattac gataagctgc tcatgcttgg c                       41

SEQ ID NO: 18           moltype = DNA   length = 42
FEATURE                 Location/Qualifiers
source                  1..42
                        mol_type = other DNA
                        organism = synthetic construct
SEQUENCE: 18
ctgatatctc gacattgctg agttaatgtc agctggggtc tc                      42

SEQ ID NO: 19           moltype = DNA   length = 23
FEATURE                 Location/Qualifiers
source                  1..23
                        mol_type = other DNA
                        organism = synthetic construct
SEQUENCE: 19
cagcaatgtc gagatatcag tgg                                           23

SEQ ID NO: 20           moltype = DNA   length = 39
FEATURE                 Location/Qualifiers
source                  1..39
                        mol_type = other DNA
                        organism = synthetic construct
SEQUENCE: 20
agaggatcta ccgagctctc atcagtgtgt ttcgggagc                          39

SEQ ID NO: 21           moltype = DNA   length = 23
FEATURE                 Location/Qualifiers
source                  1..23
                        mol_type = other DNA
                        organism = synthetic construct
SEQUENCE: 21
```

```
gagctcggta gatcctctag agt                                                 23

SEQ ID NO: 22          moltype = DNA   length = 26
FEATURE                Location/Qualifiers
source                 1..26
                       mol_type = other DNA
                       organism = synthetic construct
SEQUENCE: 22
cgtaatcatg tcatagctgt ttcctg                                              26

SEQ ID NO: 23          moltype = DNA   length = 21
FEATURE                Location/Qualifiers
source                 1..21
                       mol_type = other DNA
                       organism = synthetic construct
SEQUENCE: 23
ttgatggtgt ccgcaaaatc g                                                   21

SEQ ID NO: 24          moltype = DNA   length = 20
FEATURE                Location/Qualifiers
source                 1..20
                       mol_type = other DNA
                       organism = synthetic construct
SEQUENCE: 24
accgacacga cccataccaa                                                     20

SEQ ID NO: 25          moltype = DNA   length = 1048
FEATURE                Location/Qualifiers
source                 1..1048
                       mol_type = other DNA
                       organism = synthetic construct
SEQUENCE: 25
cgacggtatt cctgcagatg aggaaatcca cgcagccctc gaagcgatct cacatttaga        60
tgataaggct ctgctgaatc ctgcgaacat cgcgcgtgtt cttggactgc caccgaccga       120
ggaagcactt gatgagccag tcactcctcg cggctaccgc acgctcaaca gaattcctcg       180
agtgcaaaaa ttcctcatgg ataaaactcat cgtggaattc ggcaacttgg atgcactgct      240
caatgcgtca gtagaggatc taagtgcagt cgatggtgtg ggctcactgt gggcacgcca       300
catcaccgac ggacttggcc gtttaagtta ggttaaaggt caccgctggt gaagggttat       360
taccgaccac agtgtgcaag tagtagccac cggcggggac atcagtgcgg ttgttgcact       420
ggtttggcgc tgaagtggta cgagaccatg ttgcctggaa gtagcgatcc tcgccggcag       480
ggaacacgct cgtgccgtct tcaactgcag ggttgcagtc gacatcagac cagattcgtg       540
cgttggtcgc gagattgtat acctcgaaac ggagtttgtt ctcctcgagg tcaatttcgc       600
aatcaacagc agtcggatta tgcacagcca taaataattc tggctgcgca gaacctgaga       660
aagtcggctg attagtgctt gcggaaatca ccaagtcact aagctcacag gtcttttttg       720
catctgctgc aacggtggat gttgcggttg gttcagcact ggaagtctct tcttctgtgg       780
tggcttcagt cgtggattct ttagaagaag aactagacgt cgtggaagat tccattgagg       840
aggtcactac agcattattt ggctgctctt cctcaggctc cgatgatcca cctcgaagcg       900
cgacgactgc ccagataatc aaggcaatca cgacgagcag aactaggagc gctgccatgc       960
ggcggcgctt gtaaatgact tcattatgtc tcggcgttcc cacacagaac actctattac      1020
tttcatcggc ctgttcagcg gattagcg                                         1048

SEQ ID NO: 26          moltype = DNA   length = 1042
FEATURE                Location/Qualifiers
source                 1..1042
                       mol_type = other DNA
                       organism = synthetic construct
SEQUENCE: 26
aaggtctcct aaagttgatt gtggatactt caccaactgt acctttagtt acaaacttgt        60
gatttttatg aaatcaatca ctgctgccct agaggtcgat ttgcgggcct ggatttccaa       120
aagggccata gggctgagtg gcgttcaccg ccgttggaat cgattctgcg aggtcacttt       180
ttcgctgttc aggacgggaa ttgtgatagt ttccacagcg atcaaactgg tgcgccaaga       240
ttacctaaaa agccgaactt ctggcacctg tgtccggttc ccaaccggtt ctcaatctct       300
aaacctctaa accggacagg cgttccaaaa cctggaaaaa acccagagtc ttggcacgcc       360
tgtctggttt ctctaacttg agtccccga actaccaaac cacactgcca acggcccca        420
aatcaccgat cataggcaat ctcagaccga aaactaaccc acgttcttgc taattacagg       480
ttcagtacga ccgtcagaga gtcggtagcg caaaccaatg attcccaact caccggtttc       540
gaccttctga tgaatctctg gagaacggga caacagttgg tttaccgttg ccacaacgtg       600
gtgttcctcg aattccttga tggagctcag gccctctgcc ttggcttcta gaatggatgg       660
tgcaacctttt tcaaccaaaa ctcgttggta gcctccggga agtgcaccgc cttcaagtgc       720
tgctgcagtt gctgcaactg caccacagga ttccggtgccc atgacgataa ccaatggaac       780
gccgatggat tcagtggcgt attcgatgga cgcaagcact gcttggtcga ggatttctcc       840
ggcagtacga acaacaaaga ggtcaccgag accgacgtca aaaataatct caactggcac       900
tcgagaatct gaacaggaaa taacaacagc tgcaggcgtt tgtccattgc gaagtctct       960
tctgcgcggg gcgtcctggt ttggtcgatc ttcgttgaaa ctgatgaatc tttcgtttcc     1020
ggcaagcaat gcttcccata ct                                               1042

SEQ ID NO: 27          moltype = DNA   length = 42
FEATURE                Location/Qualifiers
source                 1..42
```

-continued

```
                                 mol_type = other DNA
                                 organism = synthetic construct
SEQUENCE: 27
aacagctatg acatgattac gcgacggtat tcctgcagat ga                    42

SEQ ID NO: 28        moltype = DNA  length = 33
FEATURE              Location/Qualifiers
source               1..33
                     mol_type = other DNA
                     organism = synthetic construct
SEQUENCE: 28
ctttaggaga ccttcgctaa tccgctgaac agg                              33

SEQ ID NO: 29        moltype = DNA  length = 36
FEATURE              Location/Qualifiers
source               1..36
                     mol_type = other DNA
                     organism = synthetic construct
SEQUENCE: 29
gattagcgaa ggtctcctaa agttgattgt ggatac                          36

SEQ ID NO: 30        moltype = DNA  length = 26
FEATURE              Location/Qualifiers
source               1..26
                     mol_type = other DNA
                     organism = synthetic construct
SEQUENCE: 30
agctcagtat gggaagcatt gcttgc                                      26

SEQ ID NO: 31        moltype = DNA  length = 38
FEATURE              Location/Qualifiers
source               1..38
                     mol_type = other DNA
                     organism = synthetic construct
SEQUENCE: 31
aatgcttccc atactgagct cggtagatcc tctagagt                        38

SEQ ID NO: 32        moltype = DNA  length = 26
FEATURE              Location/Qualifiers
source               1..26
                     mol_type = other DNA
                     organism = synthetic construct
SEQUENCE: 32
cgtaatcatg tcatagctgt ttcctg                                      26

SEQ ID NO: 33        moltype = DNA  length = 29
FEATURE              Location/Qualifiers
source               1..29
                     mol_type = other DNA
                     organism = synthetic construct
SEQUENCE: 33
gtgaatcaat cattgctgat taccttgtc                                   29

SEQ ID NO: 34        moltype = DNA  length = 29
FEATURE              Location/Qualifiers
source               1..29
                     mol_type = other DNA
                     organism = synthetic construct
SEQUENCE: 34
cttatgcctt tgcgtaatgt tgatagaac                                   29

SEQ ID NO: 35        moltype = DNA  length = 1000
FEATURE              Location/Qualifiers
source               1..1000
                     mol_type = other DNA
                     organism = synthetic construct
SEQUENCE: 35
aagccaccgg atttagcgca ccgacctggc agacccgcct caacgactac ctcaaggaac  60
tctcaaagtg aaaggcatca tcctcgcagg tggctccggc acccggctct accccatcac  120
caagggcatc tccaagcaac tgatgccgat ttacgacaaa cccatggtct actacccact  180
gaccacgctc attcaggccg gcatcaaaga catcctgatt atcaccaccc ctgaagacag  240
cgcctccttt gaacgcttgc ttggcgacgg ctcctcctgg ggcatcaacc tcacctacgc  300
cgtccaaccc tcccccgacg gactagccca agcattcatc atcggcgagg aattcatcgg  360
tgacgacgac gtcgcgttgg tgcttggcga taacatcttc gacggcgcac aacttggcca  420
cgcactaaag cagtgctcca accccgacgg tggcattgtc tttgcttatg aggtctccga  480
tcctgagcgt tatggcgtgg tggaatttga tgctgctaat aaggcggtgt ctattgaaga  540
aaagcccacc gcgccaaaat ccaactttgc cgtggtagga ctatatttct acgacaatcg  600
cgtggtggac atcgccaagt caatcaagcc ttcctcgcgt ggcgaactgg aaatcacctc  660
cgttaacgat gcctacctcc agcaaggtgc tttaactgtg cagcgcctgg accgtggcga  720
```

```
tgtctggtta gataccggca caatcgattc catgtccgag gcgtcttcct atgttgaggt    780
cctgcaaaaa cgtaccggca acatcatcgg atccccgaa gtcgctgcgt accgcgaagg    840
tttcatcaca gctgaagaac tcacagtgct tggtgaggaa ctgaagaaat caggctacgg    900
aaactacctg ctgagagctt tgtaatttac ggtgtggttg tggaggggtg cgtcgagaag    960
cgctcgtagg cgcttttgat ttttcggtag gctaactggg                          1000

SEQ ID NO: 36            moltype = DNA   length = 1000
FEATURE                  Location/Qualifiers
source                   1..1000
                         mol_type = other DNA
                         organism = synthetic construct
SEQUENCE: 36
ccctggcttt ggagagttac ttttaagcgg tgtcggttcc tccggcaccg cttttgggtt    60
tcaattattc aatacaagaa tttggaacca tttatatttc tcagaaatta gtaccactct    120
gattcaaaat ctaagtgatg taaaatagcc tttggattca acattttctgc tggttaatta   180
gcattctccc cacccaggtg gggatgatcc cgtcaacaag cttgttaaaa acgtcgggga    240
cgcgttctcc ccacccaggt ggggatggtc ccttttgaat gggtcggcca gctttcagcc    300
aaggatcctc cccgcgcaag tggggatgac ccccgattgc atataccaat ccagaaacag    360
aaaattgtca catgggaccg cgtgctcaat cgatatttga actttcacaa cccacgagac    420
ggcagcaaat acataaagca ataaacaagg aaaccaatcc tccaaggagc catcatggaa    480
accccatcg atccccacat ttacagcttg atgcaagacc gaaaagtagt gcgcaagaaa    540
atagctctca tactgggaat ttacatcatc gcagtcgccc tactagccta cgcaatcagc    600
tttatctttg acgacggcac acgagctgtg cttggactca tacttgtagt cgcagctttc    660
attgcaggag gtataaaatt taaagaattc atgaaaatag tagacaaatc caaccgtctc    720
actgcggaca ttaaaacagc ccaaaatagt accgcttgga aagccttaca aaaacaacaa    780
gaagaacaac agagacttat cgctgaaata ttccccgaac aacagtgact tcatcaacca    840
aatctggctg gtaattgcat tttaataatc tatgcgatga aaggcatcta aagactgtcc    900
actagcatcg ttgatctctt acgttcaggg cttaaagaca gtttcccgtc acttcccta    960
tggatgctca aggggcacgc agtaagcttg agaatcgtgt                          1000

SEQ ID NO: 37            moltype = DNA   length = 39
FEATURE                  Location/Qualifiers
source                   1..39
                         mol_type = other DNA
                         organism = synthetic construct
SEQUENCE: 37
ttacgaattc gagctcggta aagccaccgg atttagcgc                           39

SEQ ID NO: 38            moltype = DNA   length = 25
FEATURE                  Location/Qualifiers
source                   1..25
                         mol_type = other DNA
                         organism = synthetic construct
SEQUENCE: 38
cccagttagc ctaccgaaaa atcaa                                          25

SEQ ID NO: 39            moltype = DNA   length = 39
FEATURE                  Location/Qualifiers
source                   1..39
                         mol_type = other DNA
                         organism = synthetic construct
SEQUENCE: 39
ttcggtaggc taactgggcc ctggctttgg agagttact                           39

SEQ ID NO: 40            moltype = DNA   length = 34
FEATURE                  Location/Qualifiers
source                   1..34
                         mol_type = other DNA
                         organism = synthetic construct
SEQUENCE: 40
tcgactctag aacacgattc tcaagcttac tgcg                               34

SEQ ID NO: 41            moltype = DNA   length = 30
FEATURE                  Location/Qualifiers
source                   1..30
                         mol_type = other DNA
                         organism = synthetic construct
SEQUENCE: 41
agaatcgtgt tctagagtcg acctgcaggc                                    30

SEQ ID NO: 42            moltype = DNA   length = 28
FEATURE                  Location/Qualifiers
source                   1..28
                         mol_type = other DNA
                         organism = synthetic construct
SEQUENCE: 42
tttaccgagc tcgaattcgt aatcatgt                                      28

SEQ ID NO: 43            moltype = DNA   length = 19
```

```
FEATURE                   Location/Qualifiers
source                    1..19
                          mol_type = other DNA
                          organism = synthetic construct
SEQUENCE: 43
ctttcttggg aaaggcccg                                                    19

SEQ ID NO: 44             moltype = DNA   length = 21
FEATURE                   Location/Qualifiers
source                    1..21
                          mol_type = other DNA
                          organism = synthetic construct
SEQUENCE: 44
tggcacctac aacctcacca a                                                 21

SEQ ID NO: 45             moltype = DNA   length = 1053
FEATURE                   Location/Qualifiers
source                    1..1053
                          mol_type = other DNA
                          organism = synthetic construct
SEQUENCE: 45
atgaattatc agaacgacga tttacgcatc aaagaaatca aagagttact tcctcctgtc    60
gcattgctgg aaaaattccc cgctactgaa aatgccgcga atacggttgc ccatgcccga   120
aaaagcgatcc ataagatcct gaaaggtaat gatgatcgcc tgttggttgt gattggccca   180
tgctcaattc atgatcctgt cgcggcaaaa gagtatgcca ctcgcttgct ggcgctgcgt   240
gaagagctga aagatgagct ggaaatcgta atgcgcgtat attttgaaaa gccgcgtacc   300
acggtgggct ggaaagggct gattaacgat ccgcatatgg ataatagctt ccagatcaac   360
gacggtctgc gtatagcccg taaattgctg cttgatatta cgacagcgg tctgccagcg   420
gcaggtgagt ttctcgatat gatcaccca caatatctcg ctgacctgat gagctggggc   480
gcaattggcg cacgtaccac cgaatcgcag gtgcaccgcg aactggcatc agggctttct   540
tgtccggtcg gcttcaaaaa tggcaccgac ggtacgatta aagtggctat cgatgccatt   600
aatgccgccg gtgcgccgca ctgcttcctg tccgtaacga aatggggca ttcggcgatt   660
gtgaatacca gcggtaacgg cgattgccat atcattctgc gcggcggtaa agagcctaac   720
tacagcgcga agcacgttgc tgaagtgaaa gaagggctga acaaagcagg cctgccagca   780
caggtgatga tcgatttcag ccatgctaac tcgtccaaac aattcaaaaa gcagatggat   840
gtttgtgctg acgtttgcca gcagattgcc ggtggcgaaa aggccattat tggcgtgatg   900
gtggaaagcc atctggtgga aggcaatcag agcctcgaga gcggggagcc gctggcctac   960
ggtaagagca tcaccgatgc ctgcatcggc tgggaagata ccgatgctct gttacgtcaa  1020
ctggcgaatg cagtaaaagc gcgtcgcggg taa                                1053

SEQ ID NO: 46             moltype = DNA   length = 666
FEATURE                   Location/Qualifiers
source                    1..666
                          mol_type = other DNA
                          organism = synthetic construct
SEQUENCE: 46
atgggtgata ccaaagaaca gcgtattctg cgttatgttc agcagaatgc caaaccgggt    60
gatccgcaga gcgttctgga agcgattgat acctattgca cccagaaaga atgggccatg   120
aatgtgggtg atgccaaagg tcagattatg gatgccgtga ttcgtgaata tagcccgagc   180
ctggtgctgg aactgggtgc ctattgcggc tatagcgcag ttcgcatggc ccgcctgctg   240
cagccgggcg cacgcctgct gaccatggaa atgaatccgg attatgccgc aattacccag   300
cagatgctga attttgcggg tctgcaggat aaagttacca ttctgaatgg tgcatcacag   360
gatctgatcc cgcagctgaa gaaaaaatat gatgttgata ccctggatat ggtttttctg   420
gatcattgga aagatcgtta tctgccggat accctgctgc tggaaaaatg tggtctgctg   480
cgtaaaggta ccgtgctgct ggcagataat gttattgttc cgggtacccc ggattttctg   540
gcgtatgttc gtggtagcag cagctttgaa tgtacccatt atagcagcta tctggaatat   600
atgaaagtgg ttgatggtct ggaaaaagcc atttatcagg acctagtag ccctgataaa   660
tcttaa                                                               666

SEQ ID NO: 47             moltype = DNA   length = 3525
FEATURE                   Location/Qualifiers
source                    1..3525
                          mol_type = other DNA
                          organism = synthetic construct
SEQUENCE: 47
atggcagtgg attccccaga tgaacgcctg cagcgccgta ttgcacagct gtttgcagaa    60
gatgaacagg tgaaggcagc acgcccactg gaagcagtgt ctgcagcagt gtctgcacca   120
ggcatgcgtt tggcacaaat tgcagcaact gtgatggcag gctacgcaga tcgcccagca   180
gcaggtcaac gtgcatttga actgaatacc gatgatgcaa ccggccgcac ctccctgcgt   240
ctgttgccac gctttgaaac catcacctac cgcgaactgt ggcagcgcgt gggcgaagtg   300
gcagcagcat ggcatcatga tccagaaaac ccactgcgcg caggcgattt cgtggcactg   360
ctgggtttta cttctatcga ttacgcaacc ctggatctgg cagatatcca cctgggcgca   420
gtgaccgtgc cattgcaagc atctgcagca gtgtctcagc tgattgcaat cctgaccgaa   480
acctcccac gcctgctggc atctactcca gaacatctgg atgcagcagt ggaatgcctg   540
ctggcaggca ctactccaga acgtctggtg gtgtttgatt accaccagag agatgatgat   600
cagcgcgcag cattcgaatc cgcacgccgt cgtttggcag atgcaggttc tctggtgatc   660
gtggaaaccc tggatgcagt gcgcgcacgc ggtcgtgatc tgccagcagc accactgttt   720
gtgccagata ccgatgatga tccactggca ctgctgatcc acacctccgg ctctaccggt   780
accccaaagg gcgcaatgta taccaaccgc ctggcagcaa ctatgtggca gggtaactcc   840
```

```
atgctgcagg gcaactccca acgtgtgggt attaatctga actacatgcc aatgtcccac    900
atcgcaggcc gcatctcctt gtttggcgtg ctggcacgtg gtggtactgc atattttgca    960
gcaaaatccg atatgtccac cctgttcgaa gatatcggcc tggtgcgccc aaccgaaatc   1020
ttcttcgtgc cacgcgtgtg cgatatggtg ttccagcgct atcagtccga actggatcgc   1080
cgctctgtgg caggtgcaga tctggatact ctggatcgcg aagtgaaggc agatctgcgc   1140
cagaactacc tgggcggccg ttttctggtt gcagtggttg gttctgcacc actggcagca   1200
gaaatgaaga ccttcatgga atccgtgctg gatctgccac tgcacgatgg ctatggctcc   1260
accgaagcag gtgcatccgt gctgctggat aaccagatcc agcgcccacc agtgctggat   1320
tacaagctgg tggatgtgcc agaactgggc tacttccgca ccgatcgccc acatccacgt   1380
ggtgaattac tgctgaaagc agaaaccacc atcccaggct actacaagcg cccagaagtg   1440
accgcagaaa tcttcgatga agatggcttc tacaagaccg gcgatatcgt ggcagaactg   1500
gaacacgatc gcctggtgta cgtggatcgc cgcaataacg tgctgaagct gtcccagggt   1560
gaattcgtga ccgtggcaca cctggaagca gtgttcgcat cctccccact gatccgccaa   1620
attttcatct acggctcctc cgaacgctcc tacctgctgg cagtgattgt gccaaccgat   1680
gatgcactgc gcggccgtga tactgcaacc ctgaaatccg cactggcaga atccatccag   1740
cgcatcgcaa aggatgcaaa cctgcagcca tacgaaatcc cacgcgattt cctgatcgaa   1800
accgaaccat tcaccatcgc aaacggcctg ctgtccggca tagcaaaact gctgcgtcca   1860
aatctgaagg aacgctacgg cgcacagctg gaacagatgt acaccgatct gccaaccggc   1920
caggcagatg aactgctggc attgcgtcgt gaagcagcag atctgccagt gctggaaacc   1980
gtgtcccgcg cagcaaaagc aatgctgggt gtggcatctg cagatatgcg cccagatgca   2040
cacttcaccg atctgggcgg tgattccctg tccgcactgt ctttttccaa cctgctgcac   2100
gaaatcttcg gcgtggaagt gccagtgggc gtggttgtgt ctccagcaaa tgaactgcgt   2160
gatctggcaa actacatcga agcagaacgc aactccggcg caaagcgccc aacttttacc   2220
tccgtgcatg gcggcggttc cgaaatccgt gcagcagatc tgaccctgga taagttcatc   2280
gatgcacgca ccctggcagc agcagattcc attccacatg caccagtgcc agcacagact   2340
gtgctgctga ctggcgcaaa cggctatctg ggtcgtttcc tgtgtctgga atggctggaa   2400
cgcctggata agaccggcgg cactctgatt tgtgtggtgc gcggttctga tgcagcagca   2460
gcacgtaaac gcctggattc cgcattcgat tccggcgatc caggcctgct ggaacactat   2520
cagcagctgc cagcacgcac cctggaagtg ctggcaggtg atattggcga tccaaacctg   2580
ggctggatga tgcaacctg gcagcgcttg gcagaaaccg tggatctgat cgtgcaccca   2640
gcagcactgg tgaaccacgt gttaccatat acccagctgt tcggcccaaa tgtggtgggc   2700
actcagaaa tcgtgcgcct ggcaataacc gcacgccgta aaccagtgac ctatctgtct   2760
accgtgggcg tggcagatca ggtggatcca gcagaatacc aggaagattc cgatgtgcgc   2820
gaaatgtccg cagtgcgcgt ggttcgtgaa tcctatgcaa acggctacgg caactccaag   2880
tgggcaggcg aagtgctgtt gcgcgaagca catgatctgt gggcctgcc agtggcagtg   2940
tttcgttctg atatgatcct ggcacactcc cgctatgcag gccagctgaa tgtgcaggat   3000
gtgttcaccc gcctgatcct gtccctggtg gcaactggta ttgcaccata ctctttttac   3060
cgcaccgatg cagatggcaa ccgccagcgt gcacattatg atggcctgcc agcagatttc   3120
accgcagcag caattaccgc actgggcatc caagcaaccg aaggctttcg cacttacgat   3180
gtgctgaacc catacgatga tggcatctcc ctggatgaat cgtggattgg ctggtggaa    3240
tccggccacc caattcagcg tatcaccgat tattccgatt ggttccaccg cttcgaaacc   3300
gcaatccgcg cactgccaga aaagcagcgc caagcatctg tgctgccact gctggatgca   3360
taccgacatc catgccagc agtgcgcggt gcaatcctgc cagcaaaaga attccaggca    3420
gcagtgcaga ccgcaaagat cggcccagaa caggatatcc cacacctgtc cgcaccactg   3480
atcgataagt acgtgtccga tctggaactg ctgcagctgc tgtaa                   3525
```

```
SEQ ID NO: 48           moltype = DNA  length = 684
FEATURE                 Location/Qualifiers
source                  1..684
                        mol_type = other DNA
                        organism = synthetic construct
SEQUENCE: 48
atgaccgtgg gcactctggt ggcatctgtg ctgccagcaa ctgtgtttga agatctggca    60
tacgcagaac tgtactccga tccaccaggc ctgacccac tgccagaaga agcaccactg    120
atcgcacgct ccgtggcaaa acgtcgtaac gaatttatta ccgtgcgcca ctgcgcacgc    180
atcgcactgg atcaactggg tgtgccacca gcaccaattc tgaaaggcga taagggcgaa    240
ccatgctggc cagatggcat ggtgggttcc ttgactcact cgcgcaggtta ccgtggcgca    300
gtggttggcc gtcgtgatgc agtggcgctct gtgggcattg atgcagaacc acacgatgtg    360
ctgccaaacg gcgtgctgga tgcaatctcc ctgccagca aacgcgcaga tatgccacgc    420
actatgccag cagcactgca ctgggatcgc atcctgtttt gcgcaaagga agcaacctac   480
aaggcatggt tcccactgac caagcgctgg ctgggttttg aagatgcaca catcaccttc    540
gaaaccgatt ccaccggctg gaccggccgt tttgtgtctc gtattctgat cgatggctct    600
accctgtccg gccaccact gactactctg cgtggtcgtt ggtctgtgga acgtggtctg    660
gtgctgactg caatcgtgct gtaa                                           684
```

```
SEQ ID NO: 49           moltype = DNA  length = 2238
FEATURE                 Location/Qualifiers
source                  1..2238
                        mol_type = other DNA
                        organism = synthetic construct
SEQUENCE: 49
atgacttcca actttcttc cactgtcgct ggtcttcctc gcatcggagc gaagcgtgaa     60
ctgaagttcg cgctcgaagg ctactggaat ggatcaattg aaggtcgcga acttgcgcag    120
accgcccgcc aattggtcaa cactgcatcg gattctttgt ctggattgga ttccgttccg    180
tttgcaggac gttcctacta cgacgcaatg ctcgataccg ccgctatttt gggtgtgctg    240
ccggagcgtt ttgatgacat cgctgatcat gaaaacgatg gtctcccact gtggattgac    300
cgctactttg cgctgctcg cggtactgag accctgcctg cacaggcaat gaccaagtgg    360
tttgatacca actaccacta cctcgtgccg gagttgtctc cggatacacg tttcgtttttg   420
gatgcgtccg cgctgattga ggatctccgt tgccagcagg ttcgtggcgt taatgcccgc    480
```

```
cctgttctgg ttggtccact gactttcctt tcccttgctc gcaccactga tggttccaat  540
cctttggatc acctgcctgc actgtttgag gtctacgagc gcctcatcaa gtctttcgat  600
actgagtggg ttcagatcga tgagcctgcg ttggtcaccg atgttgctcc tgaggttttg  660
gagcaggtcc gcgctggtta caccactttg gctaagcgcg atggcgtgtt tgtcaatact  720
tacttcggct ctggcgatca ggcgctgaac actcttgcgg gcatcggcct tggcgcgatt  780
ggcgttgact tggtcaccca tggcgtcact gagcttgctg cgtggaaggg tgaggagctg  840
ctggttgcgg gcatcgttga tggtcgtaac atttggcgca ccgacctgtg tgctgctctt  900
gcttccctga agcgcctggc agctcgcggc ccaatcgcag tgtctacctc ttgttcactg  960
ctgcacgttc cttacaccct cgaggctgag aacattgagc ctgaggtccg cgactggctt 1020
gccttcggct cggagaagat caccgaggtc aagctgcttg ccgacgccct agccggcaac 1080
atcgacgcgg ctgcgttcga tgcggcgtcc gcagcaattg cttctcgacg cacctcccca 1140
cgcaccgcac caatcacgca ggaactccct ggccgtagcc gtggatcctt cgacactcgt 1200
gttacgctgc aggagaagtc actggagctt ccagctctgc caaccaccac cattggttct 1260
ttcccacaga ccccatccat tcgttctgct cgcgctcgtc tgcgcaagga atccatcact 1320
ttggagcagt acgaagaggc aatgcgcgaa gaaatcgatc tggtcatcgc caagcaggaa 1380
gaacttggtc ttgatgtgtt ggttcacggt gagccagagc gcaacgacat ggttcagtac 1440
ttctctgaac ttctcgacgg tttcctctca accgccaacg gctgggtcca aagctacggc 1500
tcccgctgtg ttcgtcctcc agtgttgttc ggaaacgttt cccgcccagc gccaatgact 1560
gtcaagtggt tccagtacgc acagagcctg acccagaagc atgtcaaggg aatgctcacc 1620
ggtccagtca ccatccttgc atggtccttc gttcgcgatg atcagccgct ggctaccact 1680
gctgaccagg ttgcactggc actgcgcgat gaaattaacg atctcatcga ggctggcgcg 1740
aagatcatcc aggtggatga gcctgcgatt cgtgaactgt tgccgctacg agacgtcgat 1800
aagcctgcct acctgcagtg gtccgtggac tccttccgcc tggcgactgc cggcgcaccc 1860
gacgacgtcc aaatccacac ccacatgtgc tactccgagt tcaacgaagt gatctcctcg 1920
gtcatccgct tggatgccga tgtcaccacc atcgaagcag cacgttccga catgcaggtc 1980
ctcgctgctc tgaaatcttc cggcttcgag ctcggcgtcg gacctggtgt gtgggatatc 2040
cactcccccg cgcgttcctt cgcgcaggaa gtggacggtc tcctcgaggc tgcactgcag 2100
tccgtggatc ctcgccagct gtgggtcaac ccagactgtg gtctgaagac ccgtggatgg 2160
ccagaagtgg aagcttccct aaaggttctc gttgagtccg ctaagcaggc tcgtgagaaa 2220
atcggagcaa ctatctaa                                                2238
```

```
SEQ ID NO: 50           moltype = DNA  length = 1224
FEATURE                 Location/Qualifiers
source                  1..1224
                        mol_type = other DNA
                        organism = synthetic construct
SEQUENCE: 50
gtggctcagc caaccgccgt ccgtttgttc accagtgaat ctgtaactga gggacatcca  60
gacaaaatat gtgatgctat ttccgatacc attttggacg cgctgctcga aaaagatccg  120
cagtcgcgcg tcgcagtgga aactgtggtc accaccggaa tcgtccatgt tgttggcgag  180
gtccgtacca gcgcttacgt agagatccct caattagtcc gcaacaagct catcgaaatc  240
ggattcaact cctctgaggt tggattcgac ggacgcacct gtggcgtctc agtatccatc  300
ggtgagcagt cccaggaaat cgctgacggc gtggataact ccgacgaagc cgcaccaac  360
ggcgacgttg aagaagacga ccgcgcaggt gctggcgacc agggcctgat gttcggctac  420
gccaccaacg aaaccgaaga gtacatgcct cttcctatcg cgttggcgca ccgactgtca  480
cgtcgtctga cccaggttcg taaagagggc atcgttcctc acctgcgtcc agacggaaaa  540
acccaggtca ccttcgcata cgatgcgcaa gaccgcccta cgcacctgga taccgttgtc  600
atctccaccc agcacgaccc agaagttgac cgtgcatggt tggaaaccca actgcgcgaa  660
cacgtcattg attgggtaat caaagacgca ggcattgagg atctggcaac cggtgagatc  720
accgtgttga tcaacccttc aggttccttc attctgggtg gccccatggg tgatgcgggt  780
ctgaccggcg gcaagatcat cgtggatacc tacggtgtca tggctcgca tggtggtgga  840
gcattctccg gtaaggatcc aagcaaggtg gaccgctctg ctgcatacgc catgcgttgg  900
gtagcaaaga acatcgtggc agcaggcctt gctgatcgcg ctgaagttca ggttgcatac  960
gccattggac gcgcaaagcc agtcggactt tacgttgaaa cctttgacac caacaaggaa 1020
ggcctgagcg acgagcagat tcaggctgcc gtgttggagg tctttgacct gcgtccagca 1080
gcaattatcc gtgagcttga tctgcttcgt ccgatctacg ctgacactgc tgcctacggc 1140
cactttggtc gcactgattt ggaccttcct tgggaggcta tcgaccgcgt tgatgaactt 1200
cgcgcagccc tcaagttggc ctaa                                         1224
```

```
SEQ ID NO: 51           moltype = DNA  length = 1134
FEATURE                 Location/Qualifiers
source                  1..1134
                        mol_type = other DNA
                        organism = synthetic construct
SEQUENCE: 51
atgcccaccc tcgcgccttc aggtcaactt gaaatccaag cgatcggtga tgtctccacc  60
gaagccggag caatcattac aaacgctgaa atcgcctatc accgctgggg tgaataccgc  120
gtagataaag aaggacgcag caatgtcgtt ctcatcgaac acgccctcaa tggagattcc  180
aacgcagccg attggtgggc tgacttgctc ggtcccggca aagccatcaa cactgatatt  240
tactgcgtga tctgtaccaa cgtcatcggt ggttgcaacg gttccaccgg acctggctcc  300
atgcatccag atggaaattt ctggggtaat cgcttccccg ccacgtccat tcgtgatcag  360
gtaaacgccg aaaaacaatt cctcgacgca ctcggcatca ccacggtcgc cgcagtactt  420
ggtggttcca tgggtggtgc ccgcacccta gagtgggccg caatgtaccc agaaactgtt  480
ggcgcagtcg ctgttcttgc agtttctgca cgcgccagcg cctggcaaat cggcattcaa  540
tccgcccaaa ttaaggcgat tgaaaacgac caccactggc acgaaggcaa ctactacgaa  600
tccgctgca acccagccac cggactcggc gccgcccgac gcatcgccca cctcacctac  660
cgtgtgcgaac tagaaatcga cgaacgcttc ggcaccaaag cccaaaagaa cgaaaaccca  720
ctcggtccct accgcaagcc cgaccagcgc ttcgccgtgg aatcctactt ggactaccaa  780
gcagacaagc tagtacagcg tttcgacgcc ggctcctacg tcttgctcac cgacgccctc  840
```

```
aaccgccacg acattggtcg cgaccgcgga ggcctcaaca aggcactcga atccatcaaa  900
gttccagtcc ttgtcgcagg cgtagatacc gatattttgt accccctacca ccagcaagaa  960
cacctctcca gaaacctggg aaatctactg gcaatggcaa aaatcgtatc ccctgtcggc  1020
cacgatgctt tcctcaccga aagccgccaa atggatcgca tcgtgaggaa cttcttcagc  1080
ctcatctccc cagacgaaga caaccccttcg acctacatcg agttctacat ctaa         1134

SEQ ID NO: 52              moltype = DNA   length = 1425
FEATURE                    Location/Qualifiers
source                     1..1425
                           mol_type = other DNA
                           organism = synthetic construct
SEQUENCE: 52
atggacttca aggttgccga tctttcacta gcagaggcag gacgtcacca gattcgtctt  60
gcagagtatg agatgccagg tctcatgcag ttgcgcaagg aattcgcaga cgagcagcct  120
ttgaagggcg cccgaattgc tggttctatc cacatgacgg tccagaccgc cgtgcttatt  180
gagaccctca ctgctttggg cgctgaggtt cgttgggctt cctgcaacat tttctccacc  240
caggatgagg ctgcagcggc tatcgttgtc ggctccggca ccgtcgaaga gccagctggt  300
gttccagtat tcgcgtggaa gggtgagtca ctggaggagt actggtggtg catcaaccag  360
atcttcagct ggggcgatga gctgccaaac atgatcctcg acgacggcgg tgacgccacc  420
atggctgtta ttcgcggtcg cgaatacgag caggctggtc tggttccacc agcagaggcc  480
aacgattccg atgagtacat cgcattcttg ggcatgctgc gtgaggttct tgctgcagag  540
cctggcaagt ggggcaagat cgctgaggcc gttaaggggtg tcaccgagga aaccaccacc  600
ggtgtgcacc gcctgtacca cttcgctgaa gaaggcgtgc tgcctttccc agcgatgaac  660
gtcaacgacg ctgtcaccaa gtccaagttt gataacaagt acggcacccg ccactccctg  720
atcgacggca tcaaccgcgc cactgacatg ctcatgggcg gcaagaacgt gcttgtctgc  780
ggttacggcg atgtcggcaa gggctgcgct gaggctttcg acggccaggg cgctcgcgtc  840
aaggtcaccg aagctgaccc aatcaacgct cttcaggctc tgatggatgg ctactctgtg  900
gtcaccgttg atgaggccat cgaggacgcc gacatcgtga tcaccgcgac cggcaacaag  960
gacatcattt ccttcgagca gatgctcaag atgaaggatc acgctctgct gggcaacatc  1020
ggtcactttg ataatgagat cgatatgcat tccctgttgc accgcgacga cgtcacccgc  1080
accacgatca agccacaggt cgacgagttc accttctcca ccggtcgctc catcatcgtc  1140
ctgtccgaag tcgcctgtt gaaccttggc aacgccaccg gacacccatc atttgtcatg  1200
tccaactctt tcgccgatca gaccattgcg cagatcgaac tgttccaaaa cgaaggacag  1260
tacgagaacg aggtctaccg tctgcctaag gttctcgacg aaaaggtggc acgcatccac  1320
gttgaggctc tcggcggtca gctcaccgaa ctgaccaagg agcaggctga gtacatcggc  1380
gttgacgttg caggcccatt caagccggag cactaccgct actaa               1425

SEQ ID NO: 53              moltype = DNA   length = 58
FEATURE                    Location/Qualifiers
source                     1..58
                           mol_type = other DNA
                           organism = synthetic construct
SEQUENCE: 53
taaaagcgcg tcgcgggtaa aaggaggata tacatatgtc ctcacgtaaa gagcttgc   58

SEQ ID NO: 54              moltype = DNA   length = 24
FEATURE                    Location/Qualifiers
source                     1..24
                           mol_type = other DNA
                           organism = synthetic construct
SEQUENCE: 54
ttacagcagt tcttttgctt tcgc                                        24

SEQ ID NO: 55              moltype = DNA   length = 62
FEATURE                    Location/Qualifiers
source                     1..62
                           mol_type = other DNA
                           organism = synthetic construct
SEQUENCE: 55
ggaaacagac catggaattc aaggaggata tacatatgaa ttatcagaac gacgatttac  60
gc                                                                 62

SEQ ID NO: 56              moltype = DNA   length = 20
FEATURE                    Location/Qualifiers
source                     1..20
                           mol_type = other DNA
                           organism = synthetic construct
SEQUENCE: 56
ttacccgcga cgcgcttttta                                             20

SEQ ID NO: 57              moltype = DNA   length = 59
FEATURE                    Location/Qualifiers
source                     1..59
                           mol_type = other DNA
                           organism = synthetic construct
SEQUENCE: 57
aaagcaaaag aactgctgta aaaggaggat atacatatgg gtgataccaa agaacagcg   59

SEQ ID NO: 58              moltype = DNA   length = 28
```

-continued

```
FEATURE            Location/Qualifiers
source             1..28
                   mol_type = other DNA
                   organism = synthetic construct
SEQUENCE: 58
ttaagattta tcagggctac taggtccc                                 28

SEQ ID NO: 59      moltype = DNA   length = 59
FEATURE            Location/Qualifiers
source             1..59
                   mol_type = other DNA
                   organism = synthetic construct
SEQUENCE: 59
catcgagttc tacatctaat ctagaaagga ggatatacat atggcagtgg attccccag   59

SEQ ID NO: 60      moltype = DNA   length = 21
FEATURE            Location/Qualifiers
source             1..21
                   mol_type = other DNA
                   organism = synthetic construct
SEQUENCE: 60
ttacagcagc tgcagcagtt c                                        21

SEQ ID NO: 61      moltype = DNA   length = 61
FEATURE            Location/Qualifiers
source             1..61
                   mol_type = other DNA
                   organism = synthetic construct
SEQUENCE: 61
aactgctgca gctgctgtaa ggatccccaa ggaggatata catatgaccg tgggcactct   60
g                                                             61

SEQ ID NO: 62      moltype = DNA   length = 58
FEATURE            Location/Qualifiers
source             1..58
                   mol_type = other DNA
                   organism = synthetic construct
SEQUENCE: 62
cgccaaaaca gccaagctga attcgagctc ggtaccctta cagcacgatt gcagtcag     58

SEQ ID NO: 63      moltype = DNA   length = 60
FEATURE            Location/Qualifiers
source             1..60
                   mol_type = other DNA
                   organism = synthetic construct
SEQUENCE: 63
cggagcacta ccgctactaa aaggaggata tacatatgac ttccaacttt tcttccactg   60

SEQ ID NO: 64      moltype = DNA   length = 54
FEATURE            Location/Qualifiers
source             1..54
                   mol_type = other DNA
                   organism = synthetic construct
SEQUENCE: 64
tctagaggat ccccgggtac cgagctctta gatagttgct ccgattttct cacg          54

SEQ ID NO: 65      moltype = DNA   length = 57
FEATURE            Location/Qualifiers
source             1..57
                   mol_type = other DNA
                   organism = synthetic construct
SEQUENCE: 65
ttaagcttgc atgcctgcag gtcgacaagg aggatataca tgtggctcag ccaaccg       57

SEQ ID NO: 66      moltype = DNA   length = 20
FEATURE            Location/Qualifiers
source             1..20
                   mol_type = other DNA
                   organism = synthetic construct
SEQUENCE: 66
ttaggccaac ttgagggctg                                         20

SEQ ID NO: 67      moltype = DNA   length = 50
FEATURE            Location/Qualifiers
source             1..50
                   mol_type = other DNA
                   organism = synthetic construct
SEQUENCE: 67
cagccctcaa gttggcctaa aaggaggata tacatatgcc caccctcgcg            50
```

-continued

```
SEQ ID NO: 68          moltype = DNA   length = 32
FEATURE                Location/Qualifiers
source                 1..32
                       mol_type = other DNA
                       organism = synthetic construct
SEQUENCE: 68
tctagattag atgtagaact cgatgtaggt cg                                32

SEQ ID NO: 69          moltype = DNA   length = 59
FEATURE                Location/Qualifiers
source                 1..59
                       mol_type = other DNA
                       organism = synthetic construct
SEQUENCE: 69
cctagtagcc ctgataaatc ttaaaaggag gatatacata tggacttcaa ggttgccga    59

SEQ ID NO: 70          moltype = DNA   length = 20
FEATURE                Location/Qualifiers
source                 1..20
                       mol_type = other DNA
                       organism = synthetic construct
SEQUENCE: 70
ttagtagcgg tagtgctccg                                             20

SEQ ID NO: 71          moltype = DNA   length = 22
FEATURE                Location/Qualifiers
source                 1..22
                       mol_type = other DNA
                       organism = synthetic construct
SEQUENCE: 71
tacccgggga tcctctagag tc                                           22

SEQ ID NO: 72          moltype = DNA   length = 24
FEATURE                Location/Qualifiers
source                 1..24
                       mol_type = other DNA
                       organism = synthetic construct
SEQUENCE: 72
gaattccatg gtctgtttcc tgtg                                         24

SEQ ID NO: 73          moltype = DNA   length = 25
FEATURE                Location/Qualifiers
source                 1..25
                       mol_type = other DNA
                       organism = synthetic construct
SEQUENCE: 73
cgaattcagc ttggctgttt tggcg                                        25

SEQ ID NO: 74          moltype = DNA   length = 25
FEATURE                Location/Qualifiers
source                 1..25
                       mol_type = other DNA
                       organism = synthetic construct
SEQUENCE: 74
tgcaggcatg caagcttaat taatt                                        25

SEQ ID NO: 75          moltype = DNA   length = 22
FEATURE                Location/Qualifiers
source                 1..22
                       mol_type = other DNA
                       organism = synthetic construct
SEQUENCE: 75
ggctgtgcag gtcgtaaatc ac                                           22

SEQ ID NO: 76          moltype = DNA   length = 21
FEATURE                Location/Qualifiers
source                 1..21
                       mol_type = other DNA
                       organism = synthetic construct
SEQUENCE: 76
agttccctac tctcgcatgg g                                            21

SEQ ID NO: 77          moltype = DNA   length = 22
FEATURE                Location/Qualifiers
source                 1..22
                       mol_type = other DNA
                       organism = synthetic construct
SEQUENCE: 77
```

-continued

```
ctgtggtatg gctgtgcagg tc                                         22

SEQ ID NO: 78          moltype = DNA   length = 20
FEATURE                Location/Qualifiers
source                 1..20
                       mol_type = other DNA
                       organism = synthetic construct
SEQUENCE: 78
atgcctggca gttccctact                                            20

SEQ ID NO: 79          moltype = DNA   length = 25
FEATURE                Location/Qualifiers
source                 1..25
                       mol_type = other DNA
                       organism = synthetic construct
SEQUENCE: 79
atgattgaac aagatggatt gcacg                                      25

SEQ ID NO: 80          moltype = DNA   length = 23
FEATURE                Location/Qualifiers
source                 1..23
                       mol_type = other DNA
                       organism = synthetic construct
SEQUENCE: 80
tcagaagaac tcgtcaagaa ggc                                        23

SEQ ID NO: 81          moltype = DNA   length = 20
FEATURE                Location/Qualifiers
source                 1..20
                       mol_type = other DNA
                       organism = synthetic construct
SEQUENCE: 81
cctgccactc atcgcagtac                                            20

SEQ ID NO: 82          moltype = DNA   length = 30
FEATURE                Location/Qualifiers
source                 1..30
                       mol_type = other DNA
                       organism = synthetic construct
SEQUENCE: 82
atggagaaaa aaatcactgg atataccacc                                 30

SEQ ID NO: 83          moltype = DNA   length = 2031
FEATURE                Location/Qualifiers
source                 1..2031
                       mol_type = other DNA
                       organism = synthetic construct
SEQUENCE: 83
gtggacacca aggctgtaga cactgttcgt gtcctcgctg cagacgctgt agaaaactgt    60
ggctccggcc acccaggcac cgcaatgagc ctggctcccc ttgcatacac cttgtaccag   120
cgggttatga acgtagatcc acaggacacc aactgggcag gccgtgaccg cttcgttctt   180
tcttgtggcc actcctcttt gacccagtac atccagcttt acttgggtgg attcggcctt   240
gagatggatg acctgaaggc tctgcgcacc tgggattcct tgaccccagg acaccctgag   300
taccgccaca ccaagggcgt tgagatcacc actggccctc ttggccaggg tcttgcatct   360
gcagttggta tggccatggc tgctcgtcgt gagcgtgcgc tattcgaccc aaccgctgct   420
gagggcgaat ccccattcga ccaccacatc tacgtcattg cttctgatgg tgacctgcag   480
gaaggtgtca cctctgaggc atcctccatc gctggcaccc agcagctggg caacctcatc   540
gtgttctggg atgacaaccg catctccatc gaagacaaca ctgagatcgc tttcaacgag   600
gacgttgttg ctcgttacaa ggcttacggc tggcagacca ttgaggttga ggctggcgag   660
gacgttgcag caatcgaagc tgcagtggct gaggctaaga aggacaccaa gcgacctacc   720
ttcatccgcg ttcgcaccat catcggcttc ccagctccaa ctatgatgaa caccggtgct   780
gtgcacggtg ctgctcttgg cgcagctgag gttgcagcaa ccaagactga gcttggattc   840
gatcctgagg ctcacttcgc gatcgacgat gaggttatcg ctcacacccg ctccctcgca   900
gagcgcgctg cacagaagaa ggctgcatgg caggtcaagt tcgatgagtg ggcagctgac   960
aaccctgaga acaaggctct gttcgatcgc ctgaactccc gtgagcttcc agcgggctac   1020
gctgacgagc tcccaacatg ggatgcagat gagaagggcg tcgcaactcg taaggcttcc   1080
gaggctgcac ttcaggcact gggcaagacc cttcctgagc tgtggggcgg ttccgctgac   1140
ctgcaggtt ccaacaacac cgtgatcaag ggctcccctt ccttcggccc tgagtccatc   1200
tccaccgaga cctggtctgc tgagccttac ggccgtaacc tgcacttcgg tatccgtagc   1260
cacgctatgg gatccatcct caacggcatt tccctccacg gtggcacccg cccatacggc   1320
ggaaccttcc tcatcttctc cgactacatg cgtcctgcag ttcgtcttgc agctctcatg   1380
gagaccgacg cttactacgt ctggaccac gactccatcg gtctgggcga agatggccca   1440
acccaccagc ctgttgaaac cttggctgca ctgcgcgcca tcccaggtct gtccgtcctg   1500
cgtcctgcag atgcgaacga gaccgcccag gcttgggctg cagcacttga gtacaaggaa   1560
ggccctaagg gtcttgcact gacccgccaa aacgttcctg ttctggaagg caccaaggag   1620
aaggctgcta aaggcgttcg ccgcggtggc tacgtcctgg ttgagggttc caaggaaacc   1680
ccagatgtga tcctcatggg ctccggctcc gaggttcagc ttgcagttaa cgctgcgaag   1740
gctctggaag ctgaggggcgt tgcagctcgc gttgtttccg ttccttgcat ggattgggttc   1800
caggagcagg acgcagagta catcgagtcc gttctgcctg cagctgtgac cgctcgtgtg   1860
```

-continued

```
tctgttgaag ctggcatcgc aatgccttgg taccgcttct tgggcaccca gggccgtgct   1920
gtctcccttg agcacttcgg tgcttctgcg gattaccaga ccctgtttga gaagttcggc   1980
atcaccaccg atgcagtcgt ggcagcggcc aaggactcca ttaacggtta a            2031

SEQ ID NO: 84          moltype = DNA  length = 1101
FEATURE                Location/Qualifiers
source                 1..1101
                       mol_type = other DNA
                       organism = synthetic construct
SEQUENCE: 84
atgagttctc cagtctcact cgaaaacgcg gcgtcaacca gcaacaagcg cgtcgtggct   60
ttccacgagc tgcctagccc tacagatctc atcgccgcaa acccactgac accaaagcag   120
gcttccaagg tggagcagga tcgccaggac atcgctgata tcttcgctgg cgacgatgac   180
cgcctcgttg tcgttgtggg accttgctca gttcacgatc ctgaagcagc catcgattac   240
gcaaaccgcc tggctccgct ggcaaagcgc cttgatcagg acctcaagat tgtcatcgcg   300
gtgtacttcg agaagcctcg caccatcgtc ggatggaagg gattgatcaa tgatcctcac   360
ctcaacgaaa cctacgacat cccagagggc ttgcgcattg cgcgcaaagt gcttatcgac   420
gttgtgaacc ttgatctccc agtcggctgc gaattcctcg aaccaaacag ccctcagtac   480
tacgccgaca ctgtcgcatg gggagcaatc ggcgctcgta ccaccgaatc tcaggtcac    540
cgccagctgg cttctgggat gtctatgcca attggtttca agaacggaac tgacggaaac   600
atccaggttg cagtcgacgc ggtacaggct gcccagaacc cacacttctt cttcggaacc   660
tccgacgacg gcgcgctgag cgtcgtggag accgcaggca acagcaactc ccacatcatt   720
ttgcgcggcg gtacctccgg cccgaatcat gatgcagctt cggtggaggc cgtcgtcgag   780
aagcttggtg aaaacgctcg tctcatgatc gatgcttccc atgctaactc cggcaaggat   840
catatccgac aggttgaggt tgttcgtgaa atcgcagagc agatttctgg cggttctgaa   900
gctgtgtgag gaatcatgat tgagtccttc ctcgttggtg gcgcacagaa ccttgatcct   960
gcgaaattgc gcatcaatgg cggtgaaggc ctggtgtacg gacagtctgt gaccgataag   1020
tgcatcgata ttgacaccac catcgatttg ctcgctgagc tggccgcagc agtaagggaa   1080
cgccgagcag cagccaagta a                                            1101

SEQ ID NO: 85          moltype = DNA  length = 1092
FEATURE                Location/Qualifiers
source                 1..1092
                       mol_type = other DNA
                       organism = synthetic construct
SEQUENCE: 85
atgggtagca ccgcggaaac ccagctgacc ccggtgcagg ttaccgatga tgaagccgcc   60
ctgtttgcaa tgcagctggc cagcgccagc gttctgccga tggcgctgaa aagcgccctg   120
gaactggatc tgctggaaat tatggccaaa aatggtaccc cgatgagccc gaccgaaatt   180
gcctcaaaac tgccgaccaa aaatccggaa gcaccggtga tgctggatcg tattctgcgt   240
ctgctgacct cttatagcgt gctgacctgt agcaatcgta aactgagtgg tgatggtgtg   300
gaacgcattt atggcctggg cccggtttgt aaatatctga ccaaaaatga agatggtgtt   360
agtatcgcag cgctgtgtct gatgaatcag gataaagtgc tgatggaaag ctggtatcat   420
ctgaaagatg cgattctgga tggtggcatt ccgtttaata aagcctatgg tatgagcgcc   480
tttgaatatc atggtaccga tccgcgtttt aataaagtgt ttaataatgg tatgagtaat   540
cactcaacca tcacgatgaa aaaagatcctg agacctata aaggttttga aggtctgacc   600
agcctggtgg atgtgggcgg cggcattggt gcgacccgtga aatgatcgt gtccaaatat   660
ccgaacctga aagggattaa tttcgatctg ccgcatgtta ttgaagatgc cccgtcacat   720
ccgggtattg aacatgtggg cggtgatatg tttgtgagcg ttccgaaagg tgatgccatt   780
tttatgaaat ggatctgcca cgattggagc gatgaacatt gtgtcaaatt tctgaaaaat   840
tgttatgaaa gccttccgga agatgtgcaaa gttattctgg cggagtgcat tctgccggaaa  900
accccggata gcagcctttc tacaaaacag gtggtgcatg tggattgtat tatgctggcc   960
cataatccgg gcggcaaaga acgcaccgaa aaagaatttg aagccctggc caaagcgagc   1020
ggctttaaag gcattaaagt tgtgtgcgat gcctttggtg tcaacctgat tgaactgctg   1080
aaaaaactgt aa                                                      1092

SEQ ID NO: 86          moltype = DNA  length = 3525
FEATURE                Location/Qualifiers
source                 1..3525
                       mol_type = other DNA
                       organism = synthetic construct
SEQUENCE: 86
atgtccccaa tcacccgcga agaacgcctg gaacgccgta ttcaggatct gtacgcaaac   60
gatccacagt tcgcagcagc aaagccagca accgcaatca ccgcagcaat cgaacgcccca   120
ggcttaccac tgccacaaat cattgaaacc gtgatgaccg gctacgcaga tcgcccagca   180
ctggcacaac gttccgtgga atttgtgacc gatgcaggca ccggccatac caccttacgt   240
ctgctgccaa attttgaaac catctcctac ggcgaactgt gggatcgcat ctccgcactg   300
gcagatgtgc tgtccactga acagaccgtg aagccaggca tcgcgtgtg tctgctgggt   360
tttaactccg tggattacgc aaccatcgat atgacccgtg gtcagcttca cgcagtgcca   420
gtgccactgc aaacttctgc agcaattacc cagctgcagc caatcgtggc agaaacccag   480
ccaaccatga tcgcagcatc cgtggatgca ctggcagatg caaccgaact ggcactgtcc   540
ggccagactc caactcgcgt gctggtgttt gatcatcacc gccaagtgga tgcacaccgc   600
gcagcagtgg aatctgcacg cgaacgtctg gcaggctctg cagtggtgga aactctggca   660
gaagcaatcc cacgcggcga tgtgccacgt ggtgcatctg caggttccgc accaggtact   720
gatgtgtctg atgattccct ggcactgctg atctacacct ccggctctac cggcgcacca   780
aaaggcgcaa tgtatccacg ccgcaatgtg gcaaccttct ggcgcaaacg cacctggttt   840
gaaggcggct atgaacctcc atcaccctg aacttcatgc caatgtccca cgtgatgggc   900
cgccagattc tgtacggcac tctgtgtaac ggcggcaccg catatttcgt ggcaaagtcc   960
gatctgtcca ccctgttcga agatctggca ctggtgcgcc caaccgaact gacttttgtg   1020
```

```
ccacgtgtgt gggatatggt gttcgatgaa ttccagtccg aagtggatcg ccgcctggtg    1080
gatggtgcag atcgtgttgc actggaagca caagtgaagg cagaaatccg caacgatgtg    1140
ctgggcggcc gttatacttc tgcactgact ggttctgcac caatttccga tgaaatgaag    1200
gcatgggtgg aagaactgct ggatatgcac ctggtggaag gctacggctc caccgaagca    1260
ggtatgattc tgatcgatgg cgcaatccgc cgcccagcag tgctggatta taaactggtg    1320
gatgtgccag atctgggcta cttcctgacc gatcgcccac acccacgcgg tgaactgctg    1380
gtgaaaactg attccctgtt cccaggctac taccagcgcg cagaagtgac cgcagatgtg    1440
ttcgatgcag atggcttcta ccgcaccggc gatatcatgg cagaagtggg cccagaacag    1500
ttcgtgtacc tggatcgccg caacaacgtg ctgaagctgt cccagggtga attcgtgacc    1560
gtgtccaaac tggaagcagt gttcggcgat tccccactgg tgcgccaaat ttatatctac    1620
ggcaactccg cacgcgcata cctgctggca gtgattgtgc caactcagga agcactggat    1680
gcagtgccag tggaagaact gaaggcacgc ctgggcgatt ccctgcagga agtggcaaag    1740
gcagcaggcc tgcaatccta tgaaatccca cgcgatttca tcatcgaaac caccccatgg    1800
accctggaaa acggcctgct gactggtatt cgcaagctgg cacgtccaca actgaagaag    1860
cactacggcg aactgctgga acagatctac accgatctgg cacacggcca ggcagatgaa    1920
ctgcgctctt tgcgtcaatc cggcgcagat gcaccagtgc tggtgactgt ttgtcgcgca    1980
gcagcagcac tgctgggtgg ttctgcatct gatgtgcaac cagatgcaca cttcaccgat    2040
ctgggcgacg attccctgtc tgcactgtct tttaccaacc tgctgcacga aatcttcgat    2100
atcgaagtgc cagtcgggcgt gatcgtgtcc ccagcaaatg atctgcaggc actggcagat    2160
tacgtggaag cagcacgcaa gccaggctcc tctcgcccaa cttttgcatc tgtgcatggc    2220
gcatccaacg gtcaggtgac tgaagtgcat gcaggcgatc tgtccctgga taagttcatc    2280
gatgcagcaa ccctggcaga agcaccacgc ttgccagcag caaataccca agtgcgcacc    2340
gtgctgctga ctggcgcaac tggttttctg ggccgttacc tggcactgga atggctggaa    2400
cgcatggatc tggtggatgg caagctgatc tgcctggtgc gcgcaaaatc cgataccgaa    2460
gcacgcgcac gtctggataa gaccttcgat tccggcgatc cagaactgct ggcacactac    2520
cgcgcactgg caggtgatca tctggaagtg ctggcaggcg ataaaggcga agcagatctg    2580
ggcctggatc gccagacttg gcaacgcctg gcagatactg ttgatctgat tgtggatcca    2640
gcagcactgg tgaaccacgt gctgccatat tcccagctgt tcggcccaaa tgcactgggc    2700
actgcagaac tgctgcgcct ggcattgact tctaaaatca agccatactc ctacacctcc    2760
accatcggcg tggcagatca gatcccacca tccgcattta ccgaagatgc agatatccgat    2820
gtgatctccg caacccgcgc agttgatgat tcctacgcaa acggctactc caactccaag    2880
tgggcaggcg aagtgctgct gcgcgaagca catgatctgt gcggcttgcc agtggcagtg    2940
tttcgttgtg atatgatcct ggcagatacc acctgggcag gccagttgaa tgtgccagat    3000
atgttcaccc gcatgatcct gtccctggca gcaaccggca ttgcaccagg ttcttttat    3060
gaactggcag cagatggcgc acgccagcgc gcacattatg atggcctgcc agtggaattc    3120
atcgcagaag caatctccac cctgggcgca cagtctcaag atggctttca tacctaccac    3180
gtgatgaacc catacgatga tggcatcggc ctggatgaat tcgtggattg gctgaacgaa    3240
tccggctgcc caatccagcg cattgcagat tatggcgatt ggctgcagcg cttcgaaacc    3300
gcactggcgc agatgccaga tcgccaacgt cattcttccc tgctgccact gctgcacaac    3360
taccgccaac cagaacgccc agtgcgtggc tctattgcac caaccgatcg cttccgcgca    3420
gcagtgcaag aagcaaagat tggcccagat aaggatatcc cacacgtggg cgcaccaatc    3480
atcgtgaagt acgtgtccga tctgcgcctg ctgggcctgc tgtaa                    3525
```

SEQ ID NO: 87            moltype = DNA   length = 669
FEATURE                  Location/Qualifiers
source                   1..669
                         mol_type = other DNA
                         organism = synthetic construct
SEQUENCE: 87
```
atgatcgaaa ccatcctgcc agcaggcgtg gaatccgcag aactgctgga atacccagaa    60
gatctgaagg cacacccagc agaagaacac ctgatcgaca agtccgtgga aaagcgccgc    120
cgcgatttta tcggcgcacg tcattgtgca cgcctggcac tggcagaact gggtgaacca    180
ccagtggcaa ttggcaaggg cgaacgcggt gcaccaattt ggccacgtgg tgtggtgggc    240
tctctgactc attgcgatgg ttaccgcgca gcagcagtgg cacataagat gcgctttcgc    300
tccatcggca ttgatgcaga accacacgca accctgccag aaggcgttgcat ggattccgta    360
tctctgccac cagaacgcga atggctgaag accaccgatt ccgcactgca cctggatcgc    420
ctgctgtttt gcgcaaagga agcaacctac aaggcatggt ggccactgac cgcacgctgg    480
ttgggtttg aagaagcaca cattaccttc gaaatcgagg atggctccgc agattccggc    540
aacggcactt ccattccga actgctggtg ccaggccaga ctaatgatgg cggtacccca    600
ctgctgtcct ttgatggccg ttggctgatc gcagatggct catcctgac cgcaatcgca    660
tacgcataa                                                            669
```

SEQ ID NO: 88            moltype = DNA   length = 57
FEATURE                  Location/Qualifiers
source                   1..57
                         mol_type = other DNA
                         organism = synthetic construct
SEQUENCE: 88
```
acgccgagca gcagccaagt aaaaggagga tatacatgtg gacaccaagg ctgtaga       57
```

SEQ ID NO: 89            moltype = DNA   length = 23
FEATURE                  Location/Qualifiers
source                   1..23
                         mol_type = other DNA
                         organism = synthetic construct
SEQUENCE: 89
```
ttaaccgtta atggagtcct tgg                                            23
```

SEQ ID NO: 90            moltype = DNA   length = 57

-continued

```
FEATURE                 Location/Qualifiers
source                  1..57
                        mol_type = other DNA
                        organism = synthetic construct
SEQUENCE: 90
ggaaacagac catggaattc aaggaggata tacatatgag ttctccagtc tcactcg        57

SEQ ID NO: 91           moltype = DNA   length = 18
FEATURE                 Location/Qualifiers
source                  1..18
                        mol_type = other DNA
                        organism = synthetic construct
SEQUENCE: 91
ttacttggct gctgctcg                                                   18

SEQ ID NO: 92           moltype = DNA   length = 54
FEATURE                 Location/Qualifiers
source                  1..54
                        mol_type = other DNA
                        organism = synthetic construct
SEQUENCE: 92
ccaaggactc cattaacggt taaaaggagg atatacatat gggtagcacc gcgg           54

SEQ ID NO: 93           moltype = DNA   length = 28
FEATURE                 Location/Qualifiers
source                  1..28
                        mol_type = other DNA
                        organism = synthetic construct
SEQUENCE: 93
ttacagtttt ttcagcagtt caatcagg                                        28

SEQ ID NO: 94           moltype = DNA   length = 59
FEATURE                 Location/Qualifiers
source                  1..59
                        mol_type = other DNA
                        organism = synthetic construct
SEQUENCE: 94
aagaagttac caactggtag tctagaaagg aggatataca tatgtcccca atcacccgc      59

SEQ ID NO: 95           moltype = DNA   length = 27
FEATURE                 Location/Qualifiers
source                  1..27
                        mol_type = other DNA
                        organism = synthetic construct
SEQUENCE: 95
ttggatcctt acagcaggcc cagcagg                                         27

SEQ ID NO: 96           moltype = DNA   length = 57
FEATURE                 Location/Qualifiers
source                  1..57
                        mol_type = other DNA
                        organism = synthetic construct
SEQUENCE: 96
ctgctgggcc tgctgtaagg atccaaggag gatatacata tgatcgaaac catcctg        57

SEQ ID NO: 97           moltype = DNA   length = 59
FEATURE                 Location/Qualifiers
source                  1..59
                        mol_type = other DNA
                        organism = synthetic construct
SEQUENCE: 97
cgccaaaaca gccaagctga attcgagctc ggtaccctta tgcgtatgcg attgcggtc      59

SEQ ID NO: 98           moltype = DNA   length = 60
FEATURE                 Location/Qualifiers
source                  1..60
                        mol_type = other DNA
                        organism = synthetic construct
SEQUENCE: 98
cggagcacta ccgctactaa aaggaggata tacatatgac aatattgaat cacaccctcg     60

SEQ ID NO: 99           moltype = DNA   length = 49
FEATURE                 Location/Qualifiers
source                  1..49
                        mol_type = other DNA
                        organism = synthetic construct
SEQUENCE: 99
gactctagag gatccccggg taccgagctc ttacccccga cgcaagttc                 49
```

```
SEQ ID NO: 100          moltype = DNA   length = 68
FEATURE                 Location/Qualifiers
source                  1..68
                        mol_type = other DNA
                        organism = synthetic construct
SEQUENCE: 100
ttaattaagc ttgcatgcct gcaggtcgac aaggaggata tacatatggc aaaacacctt   60
tttacgtc                                                             68

SEQ ID NO: 101          moltype = DNA   length = 19
FEATURE                 Location/Qualifiers
source                  1..19
                        mol_type = other DNA
                        organism = synthetic construct
SEQUENCE: 101
ttacttcaga ccggcagca                                                 19

SEQ ID NO: 102          moltype = DNA   length = 60
FEATURE                 Location/Qualifiers
source                  1..60
                        mol_type = other DNA
                        organism = synthetic construct
SEQUENCE: 102
gctgccggtc tgaagtaaaa ggaggatata catatgtcgc atactttaaa atcgaaaacg   60

SEQ ID NO: 103          moltype = DNA   length = 23
FEATURE                 Location/Qualifiers
source                  1..23
                        mol_type = other DNA
                        organism = synthetic construct
SEQUENCE: 103
ctaccagttg gtaacttctt cgg                                            23

SEQ ID NO: 104          moltype = DNA   length = 59
FEATURE                 Location/Qualifiers
source                  1..59
                        mol_type = other DNA
                        organism = synthetic construct
SEQUENCE: 104
attgaactgc tgaaaaaact gtaaaaggag gatatacata tggacttcaa ggttgccga    59

SEQ ID NO: 105          moltype = DNA   length = 816
FEATURE                 Location/Qualifiers
source                  1..816
                        mol_type = other DNA
                        organism = synthetic construct
SEQUENCE: 105
atgccggaag ccccgccgct gctgctggca gccgtgctgc tgggtctggt gctgctggtt   60
gttctgctgc tgctgctgcg tcattggggt tggggtctgt gcctgattgg ttggaatgaa  120
tttattctgc agccgattca taatctgctg atgggtgata ccaaagaaca gcgtattctg  180
aatcatgtgc tgcagcatgc cgaaccgggt aatgcccaga gcgtgctgga agccattgat  240
acctattgtg aacagaaaga atgggcaatg aatgtaggtg ataaaaaagg taaaatagtt  300
gatgcagtaa tccaggaaca tcagccgtca gtgctgctgg aactgggtgc ctattgcggt  360
tatagcgcag ttcgtatggc ccgtctgctg agccctggtg cacgtctgat taccattgaa  420
attaatccgg attgcgcagc cattacccag cgcatggtgg attttgcggg tgttaaagat  480
aaagtgaccc tggttgttgg tgccagccag gacattattc cgcagctgaa gaagaaatat  540
gatgttgata ccctggatat ggtgtttctg gatcattgga agatcgttac tgtgccggat  600
accctgctgt ggaagaatgc cggtctgctg cgtaaaggta ccgttctgct ggcagataat  660
gtgatttgtc cgggcgcccc ggattttctg gcgcatgttc gtggtagcag ctgctttgaa  720
tgtacccatt atcagagctt tctggaatat cgtgaagtag ttgacggttt agagaaagca  780
atttataaag gtccaggtag tgaagcgggt ccgtaa                            816

SEQ ID NO: 106          moltype = DNA   length = 675
FEATURE                 Location/Qualifiers
source                  1..675
                        mol_type = other DNA
                        organism = synthetic construct
SEQUENCE: 106
atgaagatct acggcatcta catggatcgc ccactgtccc aggaagaaaa cgaacgcttc   60
atgaccttca tctccccaga aaagcgcgaa aagtgccgcc gctttttacca caaggaagat  120
gcacaccgca ccctgctggg cgatgtgctg gtgcgttctg ttatttctcg tcaataccaa  180
ctggataagt ccgatatccg cttctccacc caggaatacg gcaagccatg catcccgatt  240
ctgccagatg cacacttcaa catctcccac tccggccgct gggtgattgg cgcatttgat  300
tcccaaccaa tcggcactcga tatcgaaaag accaagccaa tctccctgga aatcgcaaag  360
cgcttcttct ccaagaccga atactccgat ctgctggcaa aggataagga tgaacagacc  420
gattacttct accacctgtg gtccatgaag aatccttca tcaagcagga aggcaagggc  480
ctgtccctgc cactggattc ttttttccgtg cgcctgcacc aggatggcca agtgtctatt  540
gaactgccag attcccactc cccatgctac atcaagacct acgaagtgga tccaggctac  600
aagatggcag tgtgcgcagc acacccgat ttcccagaag atatcaccat ggtgtcctac  660
```

```
gaagaactgc tgtaa                                                    675

SEQ ID NO: 107           moltype = DNA   length = 64
FEATURE                  Location/Qualifiers
source                   1..64
                         mol_type = other DNA
                         organism = synthetic construct
SEQUENCE: 107
agagaagtta acaagaaata gaaggaggat atacatatga ctcaattcac tgacattgat   60
aagc                                                               64

SEQ ID NO: 108           moltype = DNA   length = 31
FEATURE                  Location/Qualifiers
source                   1..31
                         mol_type = other DNA
                         organism = synthetic construct
SEQUENCE: 108
ttagaaagct tttttcaaag gagaaattag c                                 31

SEQ ID NO: 109           moltype = DNA   length = 58
FEATURE                  Location/Qualifiers
source                   1..58
                         mol_type = other DNA
                         organism = synthetic construct
SEQUENCE: 109
ggaaacagac catggaattc aaggaggata tacatatgag tgaatctcca atgttcgc     58

SEQ ID NO: 110           moltype = DNA   length = 31
FEATURE                  Location/Qualifiers
source                   1..31
                         mol_type = other DNA
                         organism = synthetic construct
SEQUENCE: 110
ctatttcttg ttaacttctc ttctttgtct g                                 31

SEQ ID NO: 111           moltype = DNA   length = 53
FEATURE                  Location/Qualifiers
source                   1..53
                         mol_type = other DNA
                         organism = synthetic construct
SEQUENCE: 111
ctcctttgaa aaaagctttc taaaaggagg atatacatat gccggaagcc ccg          53

SEQ ID NO: 112           moltype = DNA   length = 21
FEATURE                  Location/Qualifiers
source                   1..21
                         mol_type = other DNA
                         organism = synthetic construct
SEQUENCE: 112
ttacggaccc gcttcactac c                                            21

SEQ ID NO: 113           moltype = DNA   length = 60
FEATURE                  Location/Qualifiers
source                   1..60
                         mol_type = other DNA
                         organism = synthetic construct
SEQUENCE: 113
aagaagttac caactggtag tctagaaagg aggatataca tatggcagtg gattccccag   60

SEQ ID NO: 114           moltype = DNA   length = 59
FEATURE                  Location/Qualifiers
source                   1..59
                         mol_type = other DNA
                         organism = synthetic construct
SEQUENCE: 114
ctgctgcagc tgctgtaagg atccccaagg aggatataca tatgaagatc tacggcatc    59

SEQ ID NO: 115           moltype = DNA   length = 45
FEATURE                  Location/Qualifiers
source                   1..45
                         mol_type = other DNA
                         organism = synthetic construct
SEQUENCE: 115
ctgaattcga gctcggtacc cttacagcag ttcttcgtag gacac                  45

SEQ ID NO: 116           moltype = DNA   length = 58
FEATURE                  Location/Qualifiers
source                   1..58
                         mol_type = other DNA
```

-continued

```
                        organism = synthetic construct
SEQUENCE: 116
cggagcacta ccgctactaa aaggaggata tacatatggt tcaatctgct gtcttagg      58

SEQ ID NO: 117          moltype = DNA   length = 58
FEATURE                 Location/Qualifiers
source                  1..58
                        mol_type = other DNA
                        organism = synthetic construct
SEQUENCE: 117
tctagaggat ccccgggtac cgagctctta attcttgtat tgttcacgga agtacttg      58

SEQ ID NO: 118          moltype = DNA   length = 66
FEATURE                 Location/Qualifiers
source                  1..66
                        mol_type = other DNA
                        organism = synthetic construct
SEQUENCE: 118
ttaagcttgc atgcctgcag gtcgacaagg aggatataca tatgtccaag agcaaaactt     60
tcttat                                                               66

SEQ ID NO: 119          moltype = DNA   length = 29
FEATURE                 Location/Qualifiers
source                  1..29
                        mol_type = other DNA
                        organism = synthetic construct
SEQUENCE: 119
ttaaaattcc aatttctttg gtttttccc                                      29

SEQ ID NO: 120          moltype = DNA   length = 63
FEATURE                 Location/Qualifiers
source                  1..63
                        mol_type = other DNA
                        organism = synthetic construct
SEQUENCE: 120
ccaaagaaat tggaatttta aaaggaggat atacatatgt cgcatacttt aaaatcgaaa     60
acg                                                                  63

SEQ ID NO: 121          moltype = DNA   length = 56
FEATURE                 Location/Qualifiers
source                  1..56
                        mol_type = other DNA
                        organism = synthetic construct
SEQUENCE: 121
ggtagtgaag cgggtccgta aaaggaggat atacatatgg acttcaaggt tgccga        56

SEQ ID NO: 122          moltype = DNA   length = 1053
FEATURE                 Location/Qualifiers
source                  1..1053
                        mol_type = other DNA
                        organism = synthetic construct
SEQUENCE: 122
atggccgaag aagaagcatg cctgtttgcc atgagcctgg caagcgcgag cgttctgccg     60
atggtgctga aatcagcaat tgaactggat ctgctggaac tgattgccaa agccggtccg    120
ggcgcgtatg tgagcccgag cgaactggca gcacagctgc cgacccataa tccggaagcc    180
ccgattatgc tggatcgtat tctgcgtctg ctggccacct atagtgtgct ggattgtaaa    240
ctgaataatc tggcggatgg cggtgttgaa cgtctgtatg gcctggcccc ggtttgtaaa    300
tttctgacca aaaatgccga tggcgttagc atggccccgc tgctgctgat gaaccaggat    360
aaagtgctga tggaaagctg gtatcatctg aaagatgccg ttctggatgg cggcattccg    420
tttaataaag cgtacggcat gaccgccttt gaatatcatg gcaccgatcc gcgctttaat    480
aaagttttta atcaggggat gagcaatcac tcaaccatca ccatgaagaa aattctggaa    540
gtttatcgtg gttttgaagg tctgaaaacc gttgttgatg tgggtggtgg caccggcgcc    600
accctgaata tgattattag taaatatccg accattaaag gtattaattt tgaactgccg    660
catgttgttg aagatgcccc gtcccatagc ggtgtggaac cgtatgggcg cgatatgttt    720
gtgagcgttc cgaaaggcga tgcgattttt atgaaatgga tttgccatga ttggtccgat    780
gatcattgcc gtaaactgct gaaaaaactgc taccaggccc tgccggacaa cggcaaagtg    840
attctggcag aatgcgtgct gccggaagcg ccggatacca gcctggccac ccagaatgtg    900
gttcacgttg atgtggtgat gctggcccat aatccgggcg caaagaacg taccgaaaaa     960
gaatttgaag cactggccaa aggcgccggt tttaaagaat ttcgtaaagt gtgtagcgcg    1020
gtgaataacct ggattatgga actgtgtaaa taa                                1053

SEQ ID NO: 123          moltype = DNA   length = 67
FEATURE                 Location/Qualifiers
source                  1..67
                        mol_type = other DNA
                        organism = synthetic construct
SEQUENCE: 123
caatggtgaa agtcaacgct taaaaggagg atatacatat ggatacaatt gaaaagaaat     60
cagttgc                                                              67
```

-continued

```
SEQ ID NO: 124          moltype = DNA   length = 31
FEATURE                 Location/Qualifiers
source                  1..31
                        mol_type = other DNA
                        organism = synthetic construct
SEQUENCE: 124
ttacttattg attaatgcct taactcgatt c                               31

SEQ ID NO: 125          moltype = DNA   length = 57
FEATURE                 Location/Qualifiers
source                  1..57
                        mol_type = other DNA
                        organism = synthetic construct
SEQUENCE: 125
ggaaacagac catggaattc aaggaggata tacatgag caacacagag ttagagc     57

SEQ ID NO: 126          moltype = DNA   length = 23
FEATURE                 Location/Qualifiers
source                  1..23
                        mol_type = other DNA
                        organism = synthetic construct
SEQUENCE: 126
ttaagcgttg actttcacca ttg                                        23

SEQ ID NO: 127          moltype = DNA   length = 55
FEATURE                 Location/Qualifiers
source                  1..55
                        mol_type = other DNA
                        organism = synthetic construct
SEQUENCE: 127
aggcattaat caataagtaa aaggaggata tacatggc cgaagaagaa gcatg       55

SEQ ID NO: 128          moltype = DNA   length = 31
FEATURE                 Location/Qualifiers
source                  1..31
                        mol_type = other DNA
                        organism = synthetic construct
SEQUENCE: 128
ttatttacac agttccataa tccaggtatt c                               31

SEQ ID NO: 129          moltype = DNA   length = 59
FEATURE                 Location/Qualifiers
source                  1..59
                        mol_type = other DNA
                        organism = synthetic construct
SEQUENCE: 129
tccttatgaa tgggactaat ctagaaagga ggatatacat atggcagtgg attccccag 59

SEQ ID NO: 130          moltype = DNA   length = 59
FEATURE                 Location/Qualifiers
source                  1..59
                        mol_type = other DNA
                        organism = synthetic construct
SEQUENCE: 130
cggagcacta ccgctactaa aaggaggata tacatgac aaccatcaaa acatcgaat  59

SEQ ID NO: 131          moltype = DNA   length = 51
FEATURE                 Location/Qualifiers
source                  1..51
                        mol_type = other DNA
                        organism = synthetic construct
SEQUENCE: 131
tctagaggat ccccgggtac cgagctctta tactagctgt gtctgctgtg c         51

SEQ ID NO: 132          moltype = DNA   length = 70
FEATURE                 Location/Qualifiers
source                  1..70
                        mol_type = other DNA
                        organism = synthetic construct
SEQUENCE: 132
ttaagcttgc atgcctgcag gtcgacaagg aggatataca tatgagtaaa aatcgtcgtt 60
tatttacatc                                                       70

SEQ ID NO: 133          moltype = DNA   length = 25
FEATURE                 Location/Qualifiers
source                  1..25
                        mol_type = other DNA
                        organism = synthetic construct
```

-continued

```
SEQUENCE: 133
ttattctcct aacgcttctt tacgc                                         25

SEQ ID NO: 134        moltype = DNA   length = 62
FEATURE               Location/Qualifiers
source                1..62
                      mol_type = other DNA
                      organism = synthetic construct
SEQUENCE: 134
aagaagcgtt aggagaataa aaggaggata tacatttgcc tattaatata ccaacacacc  60
tg                                                                 62

SEQ ID NO: 135        moltype = DNA   length = 27
FEATURE               Location/Qualifiers
source                1..27
                      mol_type = other DNA
                      organism = synthetic construct
SEQUENCE: 135
ttagtcccat tcataaggag tttcttg                                       27

SEQ ID NO: 136        moltype = DNA   length = 55
FEATURE               Location/Qualifiers
source                1..55
                      mol_type = other DNA
                      organism = synthetic construct
SEQUENCE: 136
ttatggaact gtgtaaataa aaggaggata tacatatgga cttcaaggtt gccga         55

SEQ ID NO: 137        moltype = DNA   length = 798
FEATURE               Location/Qualifiers
source                1..798
                      mol_type = other DNA
                      organism = synthetic construct
SEQUENCE: 137
atgctgctgg cggccgtgag tctgggtctg ctgctgctgg cctttctgct gctgctgcgt  60
catctgggtt ggggcctggt ggcgattggt tggtttgaat ttgttcagca gccggttcat 120
aatctgctga tgggtggtac caaagaacag cgtattttgc gtcatgttca gcagcatgcc 180
aaaccgggtg atccgcagag cgttctggaa gcaattgata cctattgtag tgaaaaagaa 240
tgggccatga atgttggtga tgccaaaggt cagattatgg atgcggttat tcgtgaatat 300
cgtccgagcc tggttctgga actgggcgca tattgcggtt atagcgcagt tcgcatggca 360
cgtctgctgc cgccgggtgc ccgtctgctg accatggaaa ttaatccgga ttatgccgca 420
attacccagc agatgctgga ttttgccggt ctgcaggata aagttagcat tctgattggt 480
gccagccagg atctgattcc gcagctgaag aaaaaatatg atgttgatac actggatatg 540
gtttttctgg atcattggaa agatcgttat ctgccggata ccctgctgct ggaagaatgt 600
ggtctgctgc gtaaaggtac cgttctgctg gccgataatg tgattgttcc gggtaccccg 660
gattttctgc cctatgttcg tggtagcagt agctttgaat gcacccatta ctctagctat 720
ctggaatata tgaaagttgt tgatggtctg gaaaaagcgg tgtatcaggg tccgggtagc 780
agcccggtta aaagctaa                                                798

SEQ ID NO: 138        moltype = DNA   length = 51
FEATURE               Location/Qualifiers
source                1..51
                      mol_type = other DNA
                      organism = synthetic construct
SEQUENCE: 138
aaagcaaaag aactgctgta aaaggaggat atacatatgc tgctggcggc c            51

SEQ ID NO: 139        moltype = DNA   length = 21
FEATURE               Location/Qualifiers
source                1..21
                      mol_type = other DNA
                      organism = synthetic construct
SEQUENCE: 139
ttagctttta accgggctgc t                                            21

SEQ ID NO: 140        moltype = DNA   length = 56
FEATURE               Location/Qualifiers
source                1..56
                      mol_type = other DNA
                      organism = synthetic construct
SEQUENCE: 140
agcagcccgg ttaaaagcta aaaggaggat atacatatgg acttcaaggt tgccga        56
```